US009073945B2

(12) United States Patent
Blue et al.

(10) Patent No.: US 9,073,945 B2
(45) Date of Patent: Jul. 7, 2015

(54) ALPHA-IIB-BETA-3 INHIBITORS AND USES THEREOF

(75) Inventors: Robert Blue, New York, NY (US); Barry S. Coller, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 289 days.

(21) Appl. No.: 13/441,412

(22) Filed: Apr. 6, 2012

(65) Prior Publication Data

US 2012/0190645 A1 Jul. 26, 2012

Related U.S. Application Data

(62) Division of application No. 12/514,286, filed as application No. PCT/US2007/023685 on Nov. 8, 2007, now Pat. No. 8,173,661.

(60) Provisional application No. 60/857,856, filed on Nov. 8, 2006, provisional application No. 60/873,605, filed on Dec. 7, 2006.

(51) Int. Cl.
*A01N 43/90* (2006.01)
*A61K 31/519* (2006.01)
*C07D 513/04* (2006.01)

(52) U.S. Cl.
CPC ............ *C07D 513/04* (2013.01); *A61K 31/519* (2013.01)

(58) Field of Classification Search
None
See application file for complete search history.

(56) References Cited

U.S. PATENT DOCUMENTS

| | | | |
|---|---|---|---|
| 4,265,898 A | 5/1981 | Horstmann et al. |
| 4,546,181 A | 10/1985 | Hlavka et al. |
| 4,548,938 A | 10/1985 | Kennis et al. |
| 4,985,432 A | 1/1991 | Tokunaga et al. |
| 6,179,882 B1 | 1/2001 | Vidal et al. |
| 6,492,377 B1 | 12/2002 | Blech et al. |
| 8,173,661 B2 | 5/2012 | Blue et al. |
| 2002/0071843 A1 | 6/2002 | Li et al. |
| 2006/0115514 A1 | 6/2006 | Gengrinovitch et al. |
| 2013/0251761 A1 | 9/2013 | Coller et al. |

FOREIGN PATENT DOCUMENTS

WO WO 2013/109632 7/2013

OTHER PUBLICATIONS

Khan, R.H., et al., "Condensed Heterocycles: Synthesis and Antifungal Activity of Pi-Deficient Pyrimidines Linked with Pi-Rich Heterocycles.", J. Agric. Food Chem. (1991), vol. 39, pp. 2300-2303.

Roma, et al., Bioorg Med. Chem. 11 (2003), pp. 123-138.
Dorwald, F.A. Side Reactions in Organic Synthesis, (2005), Wiley: VCH, Weinheim p. IX of Preface.
Blue et al. "Structural and therapeutic insights from the species specificity and in vivo antithrombotic activity of a novel αIIb-specific αIIbβ3 antagonist." Blood, vol. 114, Issue 1, pp. 195-201. 2009.
Blue et al. "Application of high throughput screening to identify a novel αIIb-specific small molecule inhibitor of αIIbβ3-mediated platelet interaction with fibrinogen." Blood, vol. 111, No. 3, pp. 1248-1256. 2007.
Basani et al. "Species differences in small molecule binding to αIIbβ3 are the result of sequence differences in 2 loops of the αIIb β propeller." Blood, vol. 113, pp. 902-910. 2009.
Eslin et al. "Transgenic mice studies demonstrate a role for platelet factor 4 in thrombosis: dissociation between anticoagulant and antithrombotic effect of heparin." Blood, vol. 104, pp. 3173-3180. 2004.
Law et al. "Genetic and Pharmacological Analyses of Syk Function in αIIbβ3 Signaling in Platelets." Blood, vol. 93, pp. 2645-2652. 1999.
Neyman et al. "Analysis of the spatial and temporal characteristics of platelet-delivered factor VIII-based clots." Blood, vol. 112, pp. 1101-1108. 2008.
Yarovoi et al. "Factor VIII ectopically expressed in platelets: efficacy in hemophilia A treatment." Blood, vol. 102, pp. 4006-4013. 2003.
Written Opinion of the International Searching Authority for International Application No. PCT/US11/44267. Issued Dec. 6, 2011.
Thornton et al. "Identification of distal regulatory regions in the human αIIb gene locus necessary for consistent, high-level megakaryocyte expression." Blood, vol. 100, pp. 3588-3596. 2002.
Blezdka et al. "IntegrinαIIbβ3 From Discovery to Efficacious Therapeutic Target" Circulation Research (2013) vol. 112, Issue 1, pp. 1189-1200.
Bosch et al. "Platelet Glycoprotein IIb/IIIα lockers During Percutaneous Coronary intervention and As the Initial Medical Tratment of Non-ST Segment Elevation Acute Coronary Syndromes" The Cochrane Library (2013) Issue 11, pp. 1-244, John Wiley & Sons, Ltd.
Coller, Barry S. "Blockade of Platelet GPIIb/IIIα Receptors as an Antithrombotic Strategy", Circulation (1995) vol. 92(9), pp. 2373-2380.
Cox, et al. "Integrins as Therapeutic Targets; Lessons and Opportunities", Nature Reviews Drug Discovery (2010) vol. 9, pp. 804-820.
International Search Report and Written Opinion of WO 2013/109632.
McCoy et al. "Inhibitors of Platelet Integrin αIIbβ3" Probe Reports from the NIH Molecular Libraries Program [Internet]. Bethesda (MD): National Center for Biotechnology Information (US); Mar. 27, 2010 [updated Mar. 3, 2011], pp. 1-8.

*Primary Examiner* — Jeffrey H Murray
(74) *Attorney, Agent, or Firm* — Hoxie & Associates LLC

(57) ABSTRACT

The present invention relates to methods for the treatment or prophylaxis of thrombotic disorders comprising administration of alpha-IIB-beta-3 inhibitor compounds and compositions containing the compounds. The methods of the invention are useful for the treatment or prophylaxis of thrombotic disorders, including stroke, myocardial infarction, unstable angina, peripheral vascular disease, abrupt closure following angioplasty or stent placement and thrombosis as a result of vascular surgery.

17 Claims, No Drawings

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: fibrinogen subunit

<400> SEQUENCE: 1

His His Leu Gly Gly Ala Lys Gln Ala Gly Asp Val
1               5                   10
```

ALPHA-IIB-BETA-3 INHIBITORS AND USES THEREOF

CROSS REFERENCE TO RELATED APPLICATIONS

This application is a divisional application of U.S. Ser. No. 12/514,286, filed May 8, 2009 now U.S. Pat. No. 8,173,661, which application is a national stage application filed under 35 U.S.C. §371 of International Patent Application No.: PCT/US2007/023685, filed Nov. 8, 2007, which claims priority from U.S. Provisional Application No. 60/857,856, filed on Nov. 8, 2006, and U.S. Provisional Application No. 60/873,605, filed on Dec. 7, 2006, the contents of both of which are hereby incorporated by reference in their entirety.

STATEMENT REGARDING GOVERNMENT FUNDING

This invention was made with government support under Grant No. RO119278 awarded by the National Institutes of Health. The government has certain rights in the invention.

FIELD OF THE INVENTION

The present invention relates to methods for screening compounds and compositions useful for inhibiting or reducing platelet deposition, adhesion and/or aggregation. The present invention further relates to methods of treatment or prophylaxis of thrombotic disorders, including stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.

BACKGROUND

Platelet accumulation at sites of vascular injury is a dynamic process that mediates formation of both the primary hemostatic plug and pathologic thrombus formation. The mechanisms by which platelet surface proteins direct platelet recruitment to thrombi under flow conditions have been studied in detail. In addition to directing initial platelet adhesion, cell-surface receptor interactions activate intracellular signaling. Intracellular signaling stimulates the release of thrombogenic substances from platelet granules. Signaling also mediates activation of the platelet integrin $\alpha_{IIb}\beta_3$ that facilitates firm adhesion of platelets to sites of injury.

Arterial thrombosis mediates tissue infarction in coronary artery disease, cerebrovascular disease, and peripheral vascular disease, and, thus, is the single most common cause of morbidity and mortality in the United States. Platelets are key mediators of arterial thrombosis. Thus, the identification of compounds that inhibit platelet function is of great importance to medicine.

Platelets form the body's primary means of hemostasis and, as such, have developed an elaborate mechanism of surveying the vasculature for defects in endothelial integrity. This mechanism involves the ability to respond to subendothelial matrices, shear forces, neighboring platelets, the adrenal axis, as well as soluble proteinacious, nucleotide, and lipid signals. Despite this plethora of physiologic activators, the platelet has only a small repertoire of major functional outputs. Upon activation, platelets change shape, aggregate, and secrete their granular contents. The process of platelet activation involves the expression of activities not shared by functionally intact resting platelets, including, for example, ATP release, serotonin release, lysosomal release, alpha granule release, dense granule release, and cell surface expression of markers of activated platelets (including, but not limited to P-selectin and activated GPIIb/IIIa receptor). In addition, platelet activation results in the aggregation of platelets with each other and attachment to non-platelet surrounding cells. The granular contents of platelets supply additional adhesion molecules, growth factors, coagulation enzymes and other specialized molecules instrumental in the process of thrombus formation and the initiation of the healing process.

In addition to coronary artery disease/myocardial infarction, cerebrovascular disease and peripheral vascular disease, diseases and disorders associated with inappropriate platelet activity and arterial thrombosis also include, for example, stable and unstable angina, transient ischemic attacks, placental insufficiency, unwanted thromboses subsequent to surgical procedures (e.g., aortocoronary bypass surgery, angioplasty and stent placement, and heart valve replacement), or thromboses subsequent to atrial fibrillation. Inhibitors of platelet activity can provide therapeutic and preventive benefits for each of these diseases or disorders. It is also possible that inappropriate platelet activation plays a role in venous thrombosis, such that platelet inhibitors can be useful for the treatment or prophylaxis of disorders associated with such thromboses.

A connection is emerging between platelet activation and inflammation, particularly allergic inflammation (e.g., in asthma) and inflammation at the sites of atherosclerotic damage. Therefore, compounds that inhibit platelet activation can also be useful in the treatment or prophylaxis of disorders involving inflammation.

There are a number of agents presently available that target platelet function. For example, aspirin is a relatively weak platelet inhibitor. However, aspirin can cause life-threatening allergic reactions in sensitive individuals.

Another platelet inhibiting agent is ticlopidine (Ticlid™, Roche Pharmaceuticals). Because it requires the production of active metabolites to be effective, the effect of ticlopidine is delayed 24-48 hours. The drug can also cause thrombotic thrombocytopenic purpura as well as life threatening leukopenia, nausea, abdominal pain, dyspepsia, diarrhea and skin rash.

Clopidogrel (Plavix™, Bristol-Meyers Squibb/Sanofi Pharmaceuticals) is another platelet inhibitor that requires the generation of active metabolites for its therapeutic efficacy. Therefore, clopidogrel also has a delay of 24-48 hours for its effect. Clopidogrel can also cause thrombotic thrombocytopenia purpura. The drug has also been associated with rash, edema, hypertension, hypercholesterolemia, nausea, abdominal pain, dyspepsia, diarrhea, urinary tract infections, liver enzyme elevations and arthralgia.

The platelet inhibitory agent abciximab (c7E3 Fab, Reopro®, manufacturer-Centocor B. V., distributor-Eli Lilly and Co.) is only available in a parenteral form. The drug can cause severe thrombocytopenia. Its antiplatelet effects last for several days and, therefore, may complicate surgery that is sometimes required in the setting of life-threatening arterial occlusion (e.g., emergent cardiac surgery in the setting of a myocardial infarction).

Tirofiban (Aggrastat™, Merck and Co., Inc.) is another platelet inhibitory agent that is only available in a parenteral form. Tirofiban can cause thrombocytopenia, dizziness and vasovagal reactions.

Eptifibatide (Integrilin™, COR Therapeutics, Inc., Key Pharmaceuticals Inc.) is another platelet inhibitory agent that is only available for parenteral administration. It can cause thrombocytopenia and hypotension.

There is only limited clinical experience with the oral anti-GPIIbIIIa agents, lamifiban, sibrafiban, orbofiban and xemilofiban. Similarly, clinical experience is limited with the phosphodiesterase inhibitors cilostazol, trapidil and trifusal. There is more clinical experience with the phosphodiesterase inhibitor dipyridamole, but its activity is so weak that it is not frequently used.

There is a need in the art for additional platelet adhesion and aggregation inhibitory agents for the treatment and prophylaxis of diseases or disorders associated with abnormalities in platelet adhesion and aggregation.

It is known that integrin αIIbβ3 is a receptor on the surface of human platelets. As a heterodimeric complex composed of both αIIb and β3 subunits, the dimer is responsible for binding adhesive plasma proteins, most notably fibrinogen and von Willebrand factor (vWF). The binding of fibrinogen, vWF and other ligands by αIIbβ3 is mediated principally though the peptide recognition sequence Arg-Gly-Asp (RGD) or the dodecapeptide HHLGGAKQAGDV. Currently two small molecule inhibitors of the αIIbβ3 exist: a cyclic homoarginine-glycine-aspartic acid peptide (eptifibatide) and an RGD peptidomimetic (tirofiban). Both inhibitors act by competitively blocking the binding site for fibrinogen.

Conformational changes in αIIbβ3 are thought to occur upon the binding of ligand to the receptor, leading to the exposure of ligand-induced binding sites (LIBS) as detected by LIBS-specific monoclonal antibodies (mAbs). Electron microscopy and crystal structures of the integrin in complex with various R(K)GD-like ligands support the theory that the integrin undergoes a major conformational change after or during ligand binding. It is thought that the binding of the existing small molecule αIIbβ3 inhibitors induces these conformational changes in the integrin's extracellular structure. Upon dissociation of these ligands, the integrin is thought to remain in its high affinity conformation, capable of binding circulating soluble fibrinogen, thus increasing the risk for thrombotic complications following αIIbβ3 inhibitor therapy.

SUMMARY OF THE INVENTION

We have now identified inhibitors of αIIbβ3 that are capable of inhibiting fibrinogen binding and platelet aggregation without inducing the binding of integrin β3 LIBS. The present invention thus provides pharmaceutical composition comprising αIIbβ3 antagonists, new methods of treatment and prophylaxis using αIIbβ3 antagonists, and new methods to screen for αIIbβ3 antagonists that are capable of inhibiting fibrinogen binding without inducing β3 LIBS binding.

Therefore, in one embodiment, the invention relates to 2-, 6- or 7-(substituted)-[1,3,4]thiadiazolo[3,2-a]pyrimidin-5-ones in free or salt form. In another embodiment, the invention relates to optionally 2-, 6- or 7-(substituted)-[1,3,4]oxadiazolo[3,2-a]pyrimidin-5-ones in free or salt form. In yet another embodiment, the invention relates to 2-, 5- or 6-(substituted)-[1,2,4]triazolo[1,5-a]pyrimidin-7-ones in free or salt form. In yet another embodiment, the invention relates to 2-, 5- or 6-(substituted)-pyrazolo[1,5-a]pyrimidin-7-ones in free or salt form. Collectively, these four classes of compounds shall be known as Compounds for Formula I.

More specifically, the present invention relates to compounds of Formula I-A:

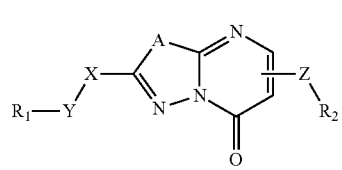

Formula I-A in free or salt form, wherein:
i) A is S, N, C, or O;
ii) X is a single bond or optionally substituted and saturated or unsaturated $C_1$-$C_4$alkylene, $C_3$-$C_{10}$cycloalkylene optionally containing one or more heteroatoms selected from a group consisting of O or N, e.g., cyclohexylene, piperazinylene or piperidinylene, —N($R_6$)— or —$C_1$-$C_4$alkyl-N($R_6$)—;
iii) Y is a single bond or optionally substituted and saturated or unsaturated $C_1$-$C_4$alkylene, optionally substituted -aryl-, (e.g., phenyl), -arylalkylene- (e.g., phenylethylene), -heteroaryl-, —C(O)—, —N($R_6$)C(O)—, —$R_3$C(O)—, —$R_3$-alkylamido- or —$R_3$—NHC(O)—;
iv) $R_1$ is $C_1$-$C_4$alkyl, $C_1$-$C_4$alkenyl, $C_1$-$C_4$alkynyl, halo$C_1$-$C_4$alkyl, aryl (e.g., phenyl), heteroaryl (e.g., pyridyl, pyrimidyl, pyridazinyl), aryl$C_1$-$C_4$alkyl- (e.g., benzyl), arylamino (e.g., phenylamino), aryl$C_1$-$C_4$alkylamino (e.g., benzylamino), $C_3$-$C_{10}$cycloalkyl optionally containing one or more heteroatoms selected from a group consisting of O or N (e.g., cyclopentyl, cyclohexyl, piperazinyl, piperidinyl, azepanyl, pyrrolidinyl, imidazolidinyl, methylpyrrolidinyl, morpholinyl, tetrahydroquinolinyl), wherein said substitutents are optionally substituted with $C_1$-$C_4$alkyl (e.g., methyl or ethyl), $C_1$-$C_4$alkoxy (e.g., methoxy), halo (e.g., Cl, Br, F, etc.), —COOH, aryl (e.g., phenyl), aryl$C_1$-$C_4$alkyl (e.g., benzyl); or
v) $R_1$ is —COOH;
vi) Z is a single bond or optionally substituted and saturated or unsaturated $C_1$-$C_4$alkylene, $C_3$-$C_8$cycloalkylene optionally containing one or more heteroatoms selected from a group consisting of O or N, e.g., cyclohexylene, piperazinylene, piperidinylene, -imidazolidine-, -pyrrolidine-;
vii) $R_2$ is optionally substituted and saturated or unsaturated $C_1$-$C_4$alkyl, $C_3$-$C_8$cycloalkyl optionally containing one or more heteroatoms selected from a group consisting of O or N (e.g., piperidinyl, piperazinyl, morpholinyl, imidazolinyl, pyrrolidinyl), aryl or heteroaryl optionally substituted with $C_1$-$C_4$alkyl, —N($R_6$)—$C_1$-$C_4$alkylaryl, nitro, halo or hydroxy group;
viii) $R_3$ is H or optionally substituted and saturated or unsaturated $C_1$-$C_4$alkyl, optionally substituted ($R_6$)N—, —($R_4$)($R_5$)N—, —N($R_4$)($R_5$)—$C_1$-$C_4$alkyl-, aryl, heteroaryl, aryl$C_1$-$C_4$alkyl, heteroaryl$C_1$-$C_4$alkyl, or $C_3$-$C_8$cycloalkyl optionally containing one or more heteroatoms selected from a group consisting of O or N (e.g., cyclopentyl, cyclohexyl, piperazinyl, methylpiperazinyl, ethylpiperazinyl, propylpiperazinyl, piperidinyl, azepanyl, pyrrolidinyl, imidazolidinyl, methylpyrrolidinyl, ethylpyrrolidinyl, morpholinyl, tetrahydroquinolinyl);
ix) $R_4$ and $R_5$ are linked together via a covalent bond so as to form a $C_3$-$C_8$ cycloalkylene containing a nitrogen atom (e.g., piperidinylene);
X) $R_6$ is H, $C_1$-$C_4$alkyl, aryl or aryl$C_1$-$C_4$alkyl,
useful for inhibiting platelet adhesion and aggregation.

The invention further provides compounds of Formula I-A as follows:

1.1 Compounds of Formula I-A, in free or salt form, wherein A is S, N, C, or O.
1.2 Compounds of Formula I-A or 1.1, in free or salt form, wherein A is S.
1.3 Compounds of Formula I-A, 1.1 or 1.2, in free or salt form, wherein X is a single bond or optionally substituted and saturated or unsaturated $C_1$-$C_4$ alkylene, $C_3$-$C_{10}$cycloalkylene optionally containing one or more heteroatoms selected from a group consisting of O or N, e.g., cyclohexylene, piperazinylene or piperidinylene, —N($R_6$)— or —$C_1$-$C_4$alkyl-N($R_6$)—;
1.4 Compounds of Formula I-A or any of 1.1-1.3, in free or salt form, wherein X is a single bond.
1.5 Compounds of Formula I-A, or any of 1.1-1.3, in free or salt form, wherein X is $C_1$-$C_4$alkylene.
1.6 Compounds of Formula I, or any of 1.1-1.3, in free or salt form, wherein X is piperazinylene.
1.7 Compounds of Formula I-A, or any of 1.1-1.3, in free or salt form, wherein X is piperidinylene.
1.8 Compounds of Formula I-A, or any of 1.1-1.3, in free or salt form, wherein X is —N($R_6$)—.
1.9 Compounds of Formula I-A, or any of 1.1-1.3, in free or salt form, wherein X is —$C_1$-$C_4$alkyl-N($R_6$)—.
1.10 Compounds of Formula I-A or any of 1.1-1.9, in free or salt form, wherein Y is a single bond or optionally substituted and saturated or unsaturated $C_1$-$C_4$alkylene, optionally substituted -aryl-, (e.g., phenyl), -heteroaryl-, —C(O)—, —N($R_6$)C(O)—, —$R_3$C(O)—, —$R_3$-alkylamido- or —$R_3$—NHC(O)—.
1.11 Compounds of Formula I-A or any of 1.1-1.10, in free or salt form, wherein Y is a single bond.
1.12 Compounds of Formula I-A or any of 1.1-1.10, in free or salt form, wherein Y is $C_1$-$C_4$alkylene.
1.13 Compounds of Formula I-A or any of 1.1-1.10, in free or salt form, wherein Y is aryl (e.g., phenyl).
1.14 Compounds of Formula I-A or any of 1.1-1.10, in free or salt form, wherein Y is —C(O)—.
1.15 Compounds of Formula I-A or any of 1.1-1.10, in free or salt form, wherein Y is —NHC(O)—.
1.16 Compounds of Formula I-A or any of 1.1-1.10, in free or salt form, wherein Y is —$R_3$—NHC(O)—.
1.17 Compounds of Formula I-A or any of 1.1-1.10, in free or salt form, wherein Y is —$R_3$-alkyl-amido-.
1.18 Compounds of Formula I-A or any of 1.1-1.17, in free or salt form, wherein $R_1$ is $C_1$-$C_4$alkyl, $C_1$-$C_4$alkenyl, $C_1$-$C_4$alkynyl, halo$C_1$-$C_4$alkyl, aryl (e.g., phenyl), heteroaryl (e.g., pyridyl, pyrimidyl, pyridazinyl), aryl$C_1$-$C_4$alkyl- (e.g., benzyl), arylamino (e.g., phenylamino), aryl$C_1$-$C_4$ alkylamino (e.g., benzylamino), $C_3$-$C_{10}$cycloalkyl optionally containing one or more heteroatoms selected from a group consisting of O or N (e.g., cyclopentyl, cyclohexyl, piperazinyl, piperidinyl, azepanyl, pyrrolidinyl, imidazolidinyl, methylpyrrolidinyl, morpholinyl, tetrahydroquinolinyl), wherein said substitutents are optionally substituted with $C_1$-$C_4$alkyl (e.g., methyl or ethyl), $C_1$-$C_4$alkoxy (e.g., methoxy), halo (e.g., Cl, Br, F, etc.), —COOH, aryl (e.g., phenyl), aryl$C_1$-$C_4$alkyl (e.g., benzyl); or $R_1$ is —COOH;
1.19 Compounds of Formula I-A or any of 1.1-1.18, in free or salt form, wherein $R_1$ is $C_1$-$C_4$alkyl optionally substituted with —COOH.
1.20 Compounds of Formula I-A or any of 1.1-1.18, in free or salt form, wherein $R_1$ is ethyl.
1.21 Compounds of Formula I-A or any of 1.1-1.18, in free or salt form, wherein $R_1$ is aryl optionally substituted with —COOH.
1.22 Compounds of Formula I-A or any of 1.1-1.18, in free or salt form, wherein $R_1$ is —COOH.
1.23 Compounds of Formula I-A or any of 1.1-1.18, in free or salt form, wherein $R_1$ is aryl, aryl$C_1$-$C_4$alkyl-, arylamino-, heteroaryl- or heteroaryl$C_1$-$C_4$alkyl-.
1.24 Compounds of Formula I-A or any of 1.1-1.23, in free or salt form, wherein Z is a single bond or optionally substituted and saturated or unsaturated $C_1$-$C_4$alkylene, $C_3$-$C_8$cycloalkylene optionally containing one or more heteroatoms selected from a group consisting of O or N, e.g., cyclohexylene, piperazinylene, piperidinylene, -imidazolidine-, -pyrrolidine-.
1.25 Compounds of Formula I-A or any of 1.1-1.24, in free or salt form, wherein Z is single bond.
1.26 Compounds of Formula I-A or any of 1.1-1.24, in free or salt form, wherein Z is a $C_1$-$C_4$alkylene.
1.27 Compounds of Formula I-A or any of 1.1-1.24, in free or salt form, wherein Z is piperidinylene or piperazinylene.
1.28 Compounds of Formula I-A or any of 1.1-1.24, in free or salt form, wherein Z is piperazinylene.
1.29 Compounds of Formula I-A or any of 1.1-1.28, in free or salt form, wherein $R_2$ is optionally substituted and saturated or unsaturated $C_1$-$C_4$ alkyl, $C_3$-$C_8$cycloalkyl optionally containing one or more heteroatoms selected from a group consisting of O or N (e.g., piperidinyl, piperazinyl, morpholinyl, imidazolinyl, pyrrolidinyl), aryl or heteroaryl optionally substituted with $C_1$-$C_4$alkyl, —N($R_6$)-$C_1$-$C_4$alkylaryl, nitro, halo or hydroxy group.
1.30 Compounds of Formula I-A or any of 1.1-1.29, in free or salt form, wherein $R_2$ is piperidinyl, piperazinyl, morpholinyl, imidazolinyl or pyrrolidinyl.
1.31 Compounds of Formula I-A or any of 1.1-1.29, in free or salt form, wherein $R_2$ is piperazinyl.
1.32 Compounds of Formula I-A or any of 1.1-1.30, in free or salt form, wherein $R_2$ is piperazin-1-yl.
1.33 Compounds of Formula I-A or any of 1.1-1.30, in free or salt form, wherein $R_2$ is $C_1$-$C_4$alkyl.
1.34 Compounds of Formula I-A or any of 1.1-1.30, in free or salt form, wherein $R_2$ is methyl.
1.35 Compounds of Formula I-A or any of 1.1-1.30, in free or salt form, wherein $R_2$ is selected from a group consisting of 2-nitro-4-chlorophenyl, 4-nitrophenyl and 3-(benzylamino)-4-nitrophenyl.
1.36 Compounds of Formula I-A or any of 1.1-1.35, in free or salt form, wherein $R_3$ is H or optionally substituted and saturated or unsaturated $C_1$-$C_4$ alkyl, optionally substituted ($R_6$)N—, —($R_4$)($R_5$)N—, —N($R_4$)($R_5$)—$C_1$-$C_4$ alkyl-, aryl, heteroaryl, aryl$C_1$-$C_4$alkyl, heteroaryl$C_1$-$C_4$alkyl, or $C_3$-$C_8$ cycloalkyl optionally containing one or more heteroatoms selected from a group consisting of O or N (e.g., cyclopentyl, cyclohexyl, piperazinyl, methylpiperazinyl, ethylpiperazinyl, propylpiperazinyl, piperidinyl, azepanyl, pyrrolidinyl, imidazolidinyl, methylpyrrolidinyl, ethylpyrrolidinyl, morpholinyl, tetrahydroquinolinyl);
1.37 Compounds of Formula I-A or any of 1.1-1.36, in free or salt form, wherein $R_4$ and $R_5$ are linked together via a covalent bond so as to form a $C_3$-$C_8$cycloalkylene containing a nitrogen atom (e.g., piperidinylene);
1.38 Compounds of Formula I-A or any of 1.1-1.37, in free or salt form, wherein $R_4$ and $R_5$ are linked together via a covalent bond so as to form a piperidinylene;

1.39 Compounds of Formula 1.38, wherein $R_4$ and $R_5$ are attached to the same nitrogen atom.

1.40 Compounds of Formula I-A or any of 1.1-1.39, in free or salt form, wherein $R_6$ is H, $C_1$-$C_4$alkyl, aryl or aryl$C_1$-$C_4$alkyl.

1.41 Compounds of Formula I-A or any of 1.1-1.40, in free or salt form, wherein $R_6$ is H.

1.42 Compounds of Formula I-A or any of 1.1-1.40, in free or salt form, wherein $R_6$ is methyl or ethyl.

In another embodiment, the invention relates to substituted 2-, 6- or 7-(N-piperazinyl or N-piperidinyl or $C_1$-$C_4$alkyl)-[1,3,4]thiadiazolo[3,2-a]pyrimidin-5-ones, preferably 2-(substituted)-7-(N-piperazinyl)-[1,3,4]thiadiazolo[3,2-a]pyrimidin-5-ones, in free or salt form. In another embodiment, the invention relates to optionally substituted 2-, 6- or 7-(N-piperazinyl or N-piperidinyl or $C_1$-$C_4$alkyl)-[1,3,4]oxadiazolo[3,2-a]pyrimidin-5-ones, preferably 2-(substituted)-7-(N-piperazinyl)-[1,3,4]oxadiazolo[3,2-a]pyrimidin-5-ones, in free or salt form. In yet another embodiment, the invention relates to optionally substituted 2-, 5- or 6-(N-piperazinyl or N-piperidinyl or $C_1$-$C_4$alkyl)-[1,2,4]triazolo[1,5-a]pyrimidin-7-ones, preferably 2-(substituted)-5-(N-piperazinyl)-[1,2,4]triazolo[1,5-a]pyrimidin-7-ones, in free or salt form. In yet another embodiment, the invention relates to optionally substituted 2-, 5- or 6-(N-piperazinyl or N-piperidinyl or $C_1$-$C_4$alkyl)-pyrazolo[1,5-a]pyrimidin-7-ones, preferably 2-(substituted)-5-(N-piperazinyl)-pyrazolo[1,5-a]pyrimidin-7-ones in free or pharmaceutically acceptable salt form. Collectively, these four sub-classes of compounds shall be known as Compounds for Formula I-B.

In another embodiment, the present invention relates to compounds of Formula I-C:

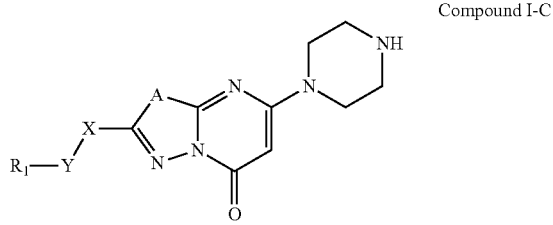

Compound I-C in free or salt form, useful for inhibiting platelet adhesion and aggregation, wherein A, X, Y and $R_1$ are as hereinbefore described.

The invention further provides compounds of Formula I-C as follows:

2.1 Compounds of Formula I-C, wherein A is S, N, C, or O;

2.2 Compounds of Formula I-C or 2.1, wherein A is S;

2.3 Compounds of Formula I-C, 2.1 or 2.2, wherein X is a single bond or optionally substituted and saturated or unsaturated $C_1$-$C_4$alkylene, $C_3$-$C_{10}$ ocycloalkylene optionally containing one or more heteroatoms selected from a group consisting of O or N, e.g., cyclohexylene, piperazinylene or piperidinylene, —N($R_6$)— or —$C_1$-$C_4$alkyl-N($R_6$)—;

2.4 Compounds of Formula I-C or any of 2.1-2.3, wherein X is —N($R_6$)—;

2.5 Compounds of Formula I-C or any of 2.1-2.4, wherein X is —N($R_6$)— and $R_6$ is H;

2.6 Compounds of Formula I-C or any of 2.1-2.5, wherein Y is a single bond or optionally substituted and saturated or unsaturated $C_1$-$C_4$alkylene, optionally substituted -aryl-, (e.g., phenyl), -arylalkylene- (e.g., phenylthethyl), -heteroaryl-, —C(O)—, —N($R_6$)C(O)—, —$R_3$C(O)—, —$R_3$-alkylamido- or —$R_3$—NHC(O)—;

2.7 Compounds of Formula I-C or any of 2.1-2.6, wherein Y is $C_1$-$C_4$alkylene;

2.8 Compounds of Formula I-C or any of 2.1-2.6, wherein Y is methylene;

2.9 Compounds of Formula I-C or any of 2.1-2.6, wherein Y is ethylene;

2.10 Compounds of Formula I-C or any of 2.1-2.6, wherein Y is n-propylene;

2.11 Compounds of Formula I-C or any of 2.1-2.6, wherein Y is -arylalkylene- 2.12 Compounds of Formula I-C or any of 2.1-2.6, wherein Y is -phenylethylene-.

2.13 Compounds of Formula I-C or any of 2.1-2.12, wherein $R_1$ is $C_1$-$C_4$alkyl, halo$C_1$-$C_4$alkyl, aryl (e.g., phenyl), heteroaryl (e.g., pyridyl, pyrimidyl, pyridazinyl), aryl$C_1$-$C_4$alkyl- (e.g., benzyl), arylamino (e.g., phenylamino), aryl$C_1$-$C_4$alkylamino (e.g., benzylamino), $C_3$-$C_{10}$cycloalkyl optionally containing one or more heteroatoms selected from a group consisting of O or N (e.g., cyclopentyl, cyclohexyl, piperazinyl, piperidinyl, azepanyl, pyrrolidinyl, imidazolidinyl, methylpyrrolidinyl, morpholinyl, tetrahydroquinolinyl), wherein said substitutents are optionally substituted with $C_1$-$C_4$alkyl (e.g., methyl or ethyl), $C_1$-$C_4$alkoxy (e.g., methoxy), halo (e.g., Cl, Br, F, etc.), —COOH, aryl (e.g., phenyl), aryl$C_1$-$C_4$alkyl (e.g., benzyl);

2.14 Compounds of Formula I-C or any of 2.1-2.13, wherein $R_1$ is aryl optionally substituted with —COOH;

2.15 Compounds of Formula I-C or any of 2.1-2.13, wherein $R_1$ is aryl substituted with —COOH;

2.16 Compounds of Formula I-C or any of 2.1-2.13, wherein $R_1$ is phenyl substituted with —COOH;

2.17 Compounds of Formula I-C or any of 2.1-2.13, wherein $R_1$ is —COOH;

2.18 Compounds of Formula I-C or any of 2.1-2.17 selected from the following:

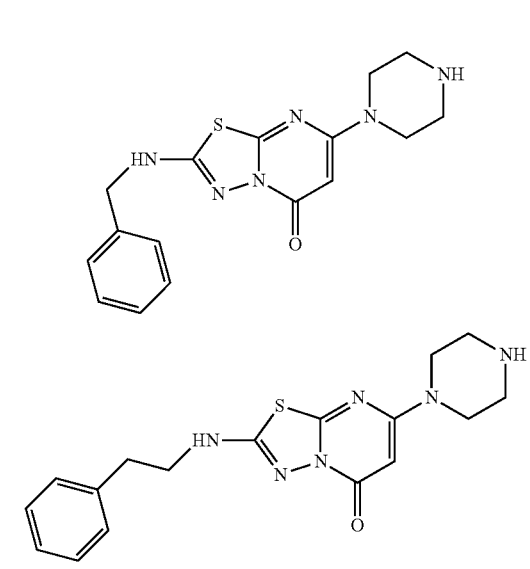

-continued

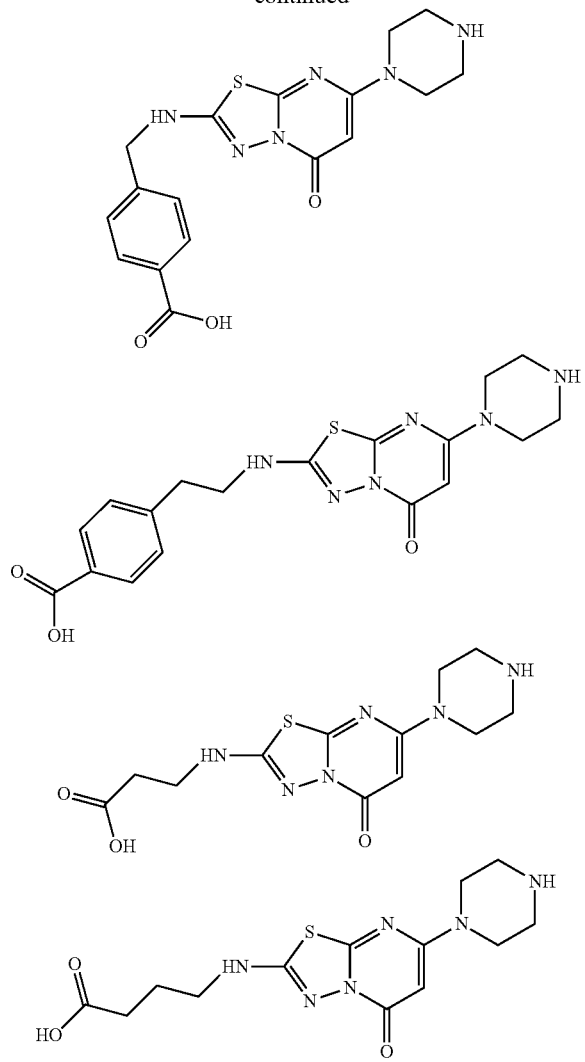

in free or salt form, useful for inhibiting platelet adhesion and aggregation.

In another embodiment, the present invention relates to compounds of Formula I-D:

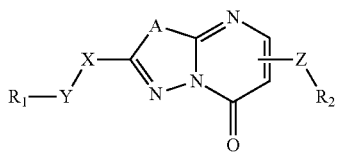

Formula I-D in free or salt form, wherein:
i) A is S or O;
ii) X is a single bond or optionally substituted and saturated or unsaturated $C_1$-$C_4$ alkylene, or $C_3$-$C_{10}$cycloalkylene optionally containing one or more heteroatoms selected from a group consisting of O or N, e.g., cyclohexylene, piperazinylene or piperidinylene;
iii) Y is a single bond or optionally substituted and saturated or unsaturated $C_1$-$C_4$ alkylene, optionally substituted -aryl-, (e.g., phenyl), -heteroaryl-, —C(O)—, —N($R_6$)C(O)—, —$R_3$C(O)—, —$R_3$-alkylamido- or —$R_3$—NHC(O)—;
iv) $R_1$ is optionally substituted $C_1$-$C_4$alkyl, $C_1$-$C_4$alkenyl, $C_1$-$C_4$alkynyl, halo$C_1$-$C_4$ alkyl, aryl (e.g., phenyl, chlorophenyl, methylphenyl, dimethylphenyl, chloro-methyl-phenyl, methoxyphenyl, dimethoxyphenyl), heteroaryl (e.g., pyridyl, pyrimidyl, pyridazinyl or methylpyridyl), aryl$C_1$-$C_4$alkyl- (e.g., benzyl), arylamino (e.g., phenylamino), aryl$C_1$-$C_4$alkylamino (e.g., benzylamino), $C_3$-$C_{10}$cycloalkyl optionally containing one or more heteroatoms selected from a group consisting of O or N (e.g., cyclopentyl, cyclohexyl, piperazinyl, methylpiperazinyl, ethylpiperazinyl, propylpiperazinyl, piperidinyl, azepanyl, pyrrolidinyl, imidazolidinyl, methylpyrrolidinyl, ethylpyrrolidinyl, morpholinyl, tetrahydroquinolinyl) or $R_1$ is optionally linked to the nitrogen atom adjacent to the carbon bearing X by a covalent bond so as to form an heteroaromatic ring, e.g., pyridyl or pyrimidyl, wherein said ring is optionally substituted with a halo group;
v) Z is a single bond or optionally substituted and saturated or unsaturated $C_1$-$C_4$ alkylene, $C_3$-$C_8$cycloalkylene optionally containing one or more heteroatoms selected from a group consisting of O or N, e.g., cyclohexylene, piperazinylene, piperidinylene, -imidazolidine-, -pyrrolidine-;
vi) $R_2$ is optionally substituted and saturated or unsaturated $C_1$-$C_4$alkyl, $C_3$-$C_8$ cycloalkyl optionally containing one or more heteroatoms selected from a group consisting of O or N (e.g., piperidinyl, piperazinyl, morpholinyl, imidazolinyl, pyrrolidinyl), aryl or heteroaryl optionally substituted with $C_1$-$C_4$ alkyl, —N($R_6$)—$C_1$-$C_4$alkylaryl, nitro, halo or hydroxy group;
vii) $R_3$ is H or optionally substituted and saturated or unsaturated $C_1$-$C_4$alkyl, optionally substituted ($R_6$)N—, —($R_4$)($R_5$)N—, —N($R_4$)($R_5$)—$C_1$-$C_4$alkyl-, aryl, heteroaryl, aryl$C_1$-$C_4$alkyl, heteroaryl$C_1$-$C_4$alkyl, or $C_3$-$C_8$cycloalkyl optionally containing one or more heteroatoms selected from a group consisting of O or N (e.g., cyclopentyl, cyclohexyl, piperazinyl, methylpiperazinyl, ethylpiperazinyl, propylpiperazinyl, piperidinyl, azepanyl, pyrrolidinyl, imidazolidinyl, methylpyrrolidinyl, ethylpyrrolidinyl, morpholinyl, tetrahydroquinolinyl);
viii) $R_4$ and $R_5$ are linked together via a covalent bond so as to form a cycloalkylene containing a nitrogen atom (e.g., piperidinylene);
ix) $R_6$ is H, $C_{1-4}$alkyl, aryl or arylalkyl,
useful for inhibiting platelet adhesion and aggregation.

The invention further provides compounds of Formula I-D as follows:
3.1 Compounds of Formula I-D, in free or salt form, wherein A is S or O;
3.2 Compounds of Formula I-D or 3.1, in free or salt form, wherein A is S.
3.3 Compounds of Formula I-D, 3.1 or 3.2, in free or salt form, wherein X is a single bond or optionally substituted and saturated or unsaturated $C_1$-$C_4$ alkylene, or $C_3$-$C_{10}$cycloalkylene optionally containing one or more heteroatoms selected from a group consisting of O or N, e.g., cyclohexylene, piperazinylene or piperidinylene;
3.4 Compounds of Formula I-D or any of 3.1-3.3, in free or salt form, wherein X is a single bond.
3.5 Compounds of Formula I-D, or any of 3.1-3.3, in free or salt form, wherein X is $C_1$-$C_4$alkylene.

3.6 Compounds of Formula I-D, or any of 3.1-3.3, in free or salt form, wherein X is piperazinylene.

3.7 Compounds of Formula I-D, or any of 3.1-3.3, in free or salt form, wherein X is piperidinylene.

3.8 Compounds of Formula I-D or any of 3.1-3.7, in free or salt form, wherein Y is a single bond or optionally substituted and saturated or unsaturated $C_1$-$C_4$alkylene, optionally substituted -aryl-, (e.g., phenyl), -heteroaryl-, —C(O)—, —N($R_6$)C(O)—, —$R_3$C(O)—, —$R_3$-alkylamido- or —$R_3$—NHC(O)—.

3.9 Compounds of Formula I-C or any of 3.1-3.8, in free or salt form, wherein Y is a single bond.

3.10 Compounds of Formula I-D or any of 3.1-3.8, in free or salt form, wherein Y is $C_1$-$C_4$alkylene (e.g., ethylene or n-propylene)

3.11 Compounds of Formula I-D or any of 3.1-3.8, in free or salt form, wherein Y is aryl (e.g., phenyl).

3.12 Compounds of Formula I-D or any of 3.1-3.8, in free or salt form, wherein Y is —C(O)—.

3.13 Compounds of Formula I-D or any of 3.1-3.8, in free or salt form, wherein Y is —NHC(O)—.

3.14 Compounds of Formula I-D or any of 3.1-3.8, in free or salt form, wherein Y is —$R_3$—NHC(O)—.

3.15 Compounds of Formula I-D or any of 3.1-3.8, in free or salt form, wherein Y is —$R_3$-alkyl-amido-.

3.16 Compounds of Formula I-D or any of 3.1-3.15, in free or salt form, wherein $R_1$ is optionally substituted $C_1$-$C_4$alkyl, $C_1$-$C_4$alkenyl, $C_1$-$C_4$ alkynyl, halo$C_1$-$C_4$alkyl, aryl (e.g., phenyl, chlorophenyl, methylphenyl, dimethylphenyl, chloro-methyl-phenyl, methoxyphenyl, dimethoxyphenyl), heteroaryl (e.g., pyridyl, pyrimidyl, pyridazinyl or methylpyridyl), aryl$C_1$-$C_4$alkyl- (e.g., benzyl), arylamino (e.g., phenylamino), aryl$C_1$-$C_4$alkylamino (e.g., benzylamino), $C_3$-$C_{10}$cycloalkyl optionally containing one or more heteroatoms selected from a group consisting of O or N (e.g., cyclopentyl, cyclohexyl, piperazinyl, methylpiperazinyl, ethylpiperazinyl, propylpiperazinyl, piperidinyl, azepanyl, pyrrolidinyl, imidazolidinyl, methylpyrrolidinyl, ethylpyrrolidinyl, morpholinyl, tetrahydroquinolinyl) or $R_1$ is optionally linked to the nitrogen atom adjacent to the carbon bearing X by a covalent bond so as to form an heteroaromatic ring, e.g., pyridyl or pyrimidyl, wherein said ring is optionally substituted with a halo group;

3.17 Compounds of Formula I-D or any of 3.1-3.16, in free or salt form, wherein $R_1$ is $C_1$-$C_4$alkyl.

3.18 Compounds of Formula I-D or any of 3.1-3.16, in free or salt form, wherein $R_1$ is ethyl.

3.19 Compounds of Formula I-D or any of 3.1-3.16, in free or salt form, wherein $R_1$ is aryl, arylamino-, arylalkyl-, heteroaryl- or heteroarylalkyl-.

3.20 Compounds of Formula I-C or any of 3.1-3.19, in free or salt form, wherein Z is a single bond or optionally substituted and saturated or unsaturated $C_1$-$C_4$alkylene, $C_3$-$C_8$cycloalkylene optionally containing one or more heteroatoms selected from a group consisting of O or N, e.g., cyclohexylene, piperazinylene, piperidinylene, -imidazolidine-, -pyrrolidine-.

3.21 Compounds of Formula I-D or any of 3.1-3.20, in free or salt form, wherein Z is single bond.

3.22 Compounds of Formula I-D or any of 3.1-3.20, in free or salt form, wherein Z is a $C_1$-$C_4$alkylene.

3.23 Compounds of Formula I-D or any of 3.1-3.20, in free or salt form, wherein Z is piperidinylene.

3.24 Compounds of Formula I-D or any of 3.1-3.20, in free or salt form, wherein Z is piperazinylene.

3.25 Compounds of Formula I-D or any of 3.1-3.24, in free or salt form, wherein $R_2$ is optionally substituted and saturated or unsaturated $C_1$-$C_4$ alkyl, $C_3$-$C_8$cycloalkyl optionally containing one or more heteroatoms selected from a group consisting of O or N (e.g., piperidinyl, piperazinyl, morpholinyl, imidazolinyl, pyrrolidinyl), aryl or heteroaryl optionally substituted with $C_1$-$C_4$alkyl, —N($R_6$)-$C_1$-$C_4$alkylaryl, nitro, halo or hydroxy group.

3.26 Compounds of Formula I-D or any of 3.1-3.25, in free or salt form, wherein $R_2$ is piperidinyl, piperazinyl, morpholinyl, imidazolinyl or pyrrolidinyl.

3.27 Compounds of Formula I-D or any of 3.1-3.26, in free or salt form, wherein $R_2$ is piperazinyl.

3.28 Compounds of Formula I-D or any of 3.1-1.27, in free or salt form, wherein $R_2$ is piperazin-1-yl.

3.29 Compounds of Formula I-D or any of 3.1-1.25, in free or salt form, wherein $R_2$ is methyl.

3.30 Compounds of Formula I-D or any of 3.1-3.29, in free or salt form, wherein $R_3$ is H or optionally substituted and saturated or unsaturated $C_1$-$C_4$ alkyl, optionally substituted —($R_6$)N—, —($R_4$)($R_5$)N—, —N($R_4$)($R_5$)—$C_1$-$C_4$ alkyl-, aryl, heteroaryl, aryl$C_1$-$C_4$alkyl, heteroaryl$C_1$-$C_4$alkyl, or $C_3$-$C_8$ cycloalkyl optionally containing one or more heteroatoms selected from a group consisting of O or N (e.g., cyclopentyl, cyclohexyl, piperazinyl, methylpiperazinyl, ethylpiperazinyl, propylpiperazinyl, piperidinyl, azepanyl, pyrrolidinyl, imidazolidinyl, methylpyrrolidinyl, ethylpyrrolidinyl, morpholinyl, tetrahydroquinolinyl);

3.31 Compounds of Formula I-D or any of 3.1-3.30, in free or salt form, wherein $R_4$ and $R_5$ are linked together via a covalent bond so as to form a $C_3$-$C_8$cycloalkylene containing a nitrogen atom;

3.32 Compounds of Formula I-D or any of 3.1-3.31, in free or salt form, wherein $R_4$ and $R_5$ are linked together via a covalent bond so as to form a piperidinylene;

3.33 Compounds of 3.32, in free or salt form, wherein $R_4$ and $R_5$ are attached to the same nitrogen atom.

3.34 Compounds of Formula I-D or any of 3.1-3.33, in free or salt form, wherein $R_6$ is H, $C_{1-4}$alkyl, aryl or arylalkyl.

3.35 Compounds of Formula I-D or any of 3.1-3.34, in free or salt form, wherein $R_6$ is H.

3.36 Compounds of Formula I-D or any of 3.1-3.34, in free or salt form, wherein $R_6$ is methyl or ethyl.

In another embodiment, the present invention relates to compounds of Formula I-E:

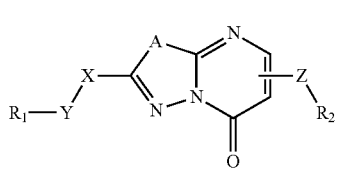

Formula I-E in free or salt form, wherein:
i) A is S or O;
ii) X is a single bond or optionally substituted and saturated or unsaturated $C_1$-$C_4$ alkylene or $C_3$-$C_{10}$cycloalkylene optionally containing one or more heteroatoms selected from a group consisting of O or N, e.g., cyclohexylene, piperazinylene or piperidinylene;
iii) Y is a single bond or optionally substituted and saturated or unsaturated $C_1$-$C_4$ alkylene, optionally substituted -aryl-, (e.g., phenyl), -heteroaryl-, —C(O)—, —N($R_3$)C(O)—, —$R_3$C(O)—, —$R_3$-alkylamido- or —$R_3$—NHC(O)—;

iv) $R_1$ is optionally substituted $C_1$-$C_4$alkyl, $C_1$-$C_4$alkenyl, $C_1$-$C_4$alkynyl, haloalkyl, aryl (e.g., phenyl, chlorophenyl, methylphenyl, dimethylphenyl, chloro-methyl-phenyl, benzyl, methoxyphenyl, dimethoxyphenyl), heteroaryl (e.g., pyridyl, pyrimidyl, pyridazinyl or methylpyridyl), arylamino (e.g., phenylamino), arylalkylamino (e.g., benzylamino), $C_3$-$C_{10}$cycloalkyl optionally containing one or more heteroatoms selected from a group consisting of O or N (e.g., cyclopentyl, cyclohexyl, piperazinyl, methylpiperazinyl, ethylpiperazinyl, propylpiperazinyl, piperidinyl, azepanyl, pyrrolidinyl, imidazolidinyl, methylpyrrolidinyl, ethylpyrrolidinyl, morpholinyl, tetrahydroquinolinyl), or $R_1$ is optionally linked to the nitrogen atom adjacent to the carbon bearing X by a covalent bond so as to form an heteroaromatic ring, e.g., pyridyl or pyrimidyl, wherein said ring is optionally substituted with a halo group;

v) Z is a single bond or optionally substituted and saturated or unsaturated $C_1$-$C_4$ alkylene, $C_3$-$C_8$cycloalkylene optionally containing one or more heteroatoms selected from a group consisting of O or N, e.g., cyclohexylene, piperazinylene, piperidinylene, -imidazolidine-, -pyrrolidine-;

vi) $R_2$ is optionally substituted and saturated or unsaturated $C_1$-$C_4$alkyl, $C_3$-$C_8$ cycloalkyl optionally containing one or more heteroatoms selected from a group consisting of O or N (e.g., piperidinyl, piperazinyl, morpholinyl, imidazolinyl, pyrrolidinyl), or $R_2$ is aryl or heteroaryl optionally substituted with $C_1$-$C_4$alky, —N($R_5$)-alkylaryl, nitro, halo or hydroxy group;

vii) $R_3$ is H or optionally substituted and saturated or unsaturated $C_1$-$C_4$alkyl, optionally substituted ($R_4$)($R_5$)N—, —N($R_4$)($R_5$)alkyl-, aryl, heteroaryl, arylalkyl, heteroarylalkyl, or $C_3$-$C_8$cycloalkyl optionally containing one or more heteroatoms selected from a group consisting of O or N (e.g., cyclopentyl, cyclohexyl, piperazinyl, methylpiperazinyl, ethylpiperazinyl, propylpiperazinyl, piperidinyl, azepanyl, pyrrolidinyl, imidazolidinyl, methylpyrrolidinyl, ethylpyrrolidinyl, morpholinyl, tetrahydroquinolinyl);

viii) $R_4$ and $R_5$ are independently H, optionally substituted $C_1$-$C_4$alkyl, or $R_4$ and $R_5$ are linked together via a covalent bond so as to form a cycloalkylene containing at least one heteroatom selected from a group consisting of N and O (e.g., piperidinylene or piperazinylene), useful for inhibiting platelet adhesion and aggregation.

The invention further provides compounds of Formula I-E as follows:

4.1 Compounds of Formula I-E, in free or salt form, wherein A is S or O.

4.2 Compounds of Formula I-E or 4.1, in free or salt form, wherein A is S.

4.3 Compounds of Formula I-E, 4.1 or 4.2, in free or salt form, wherein X is a single bond or optionally substituted and saturated or unsaturated $C_1$-$C_4$ alkylene or $C_3$-$C_{10}$cycloalkylene optionally containing one or more heteroatoms selected from a group consisting of O or N (e.g., cyclohexylene, piperazinylene or piperidinylene).

4.4 Compounds of Formula I-E or any of 4.1-4.3, in free or salt form, wherein X is a single bond.

4.5 Compounds of Formula I-E, or any of 4.1-4.3 in free or salt form, wherein X is $C_1$-$C_4$alkylene.

4.6 Compounds of Formula I-E, or any of 4.1-4.3, in free or salt form, wherein X is piperidinylene.

4.7 Compounds of Formula I-E or any of 4.1-4.6, in free or salt form, wherein Y is a single bond or optionally substituted and/or saturated or unsaturated $C_1$-$C_4$alkylene, -aryl-, (e.g., phenyl), -heteroaryl-, —C(O)—, —N($R_3$)C(O)—, —$R_3$C(O)—, —$R_3$-alkylamido- or —$R_3$—NHC(O)—;

4.8 Compounds of Formula I-E or any of 4.1-4.6, in free or salt form, wherein Y is a single bond.

4.9 Compounds of Formula I-E or any of 4.1-4.6, in free or salt form, wherein Y is $C_1$-$C_4$methylene.

4.10 Compounds of Formula I-E or any of 4.1-4.6, in free or salt form, wherein Y is —C(O)—.

4.11 Compounds of Formula I-E or any of 4.1-4.6, in free or salt form, wherein Y is —NHC(O)—.

4.12 Compounds of Formula I-E or any of 4.1-4.6, in free or salt form, wherein Y is —$R_3$—NHC(O)—.

4.13 Compounds of Formula I-E or any of 4.1-4.6, in free or salt form, wherein Y is —$R_3$-alkyl-amido-.

4.14 Compounds of Formula I-E or any of 4.1-4.13, in free or salt form, wherein $R_1$ is optionally substituted $C_1$-$C_4$alkyl, $C_1$-$C_4$alkenyl, $C_1$-$C_4$ alkynyl, haloalkyl, aryl (e.g., phenyl, chlorophenyl, methylphenyl, dimethylphenyl, chloro-methyl-phenyl, benzyl, methoxyphenyl, dimethoxyphenyl), heteroaryl (e.g., pyridyl, pyrimidyl, pyridazinyl or methylpyridyl), arylamino (e.g., phenylamino), arylalkylamino (e.g., benzylamino), $C_3$-$C_{10}$cycloalkyl optionally containing one or more heteroatoms selected from a group consisting of O or N (e.g., cyclopentyl, cyclohexyl, piperazinyl, methylpiperazinyl, ethylpiperazinyl, propylpiperazinyl, piperidinyl, azepanyl, pyrrolidinyl, imidazolidinyl, methylpyrrolidinyl, ethylpyrrolidinyl, morpholinyl, tetrahydroquinolinyl), or $R_1$ is optionally linked to the nitrogen atom adjacent to the carbon bearing X by a covalent bond so as to form an heteroaromatic ring, e.g., pyridyl or pyrimidyl, wherein said ring is optionally substituted with a halo group.

4.15 Compounds of Formula I-E or any of 4.1-4.14, in free or salt form, wherein $R_1$ is saturated or unsaturated $C_1$-$C_4$alkyl.

4.16 Compounds of Formula I-E or any of 2.1-4.15, in free or salt form, wherein $R_1$ is ethyl.

4.17 Compounds of Formula I-E or any of 4.1-4.14, in free or salt form, wherein $R_1$ is aryl, arylamino, arylalkyl, heteroaryl or heteroarylalkyl.

4.18 Compounds of Formula I-E or any of 4.1-4.17, in free or salt form, wherein Z is a single bond or optionally substituted and saturated or unsaturated $C_1$-$C_4$alkylene, $C_3$-$C_8$cycloalkylene optionally containing one or more heteroatoms selected from a group consisting of O or N (e.g., cyclohexylene, piperazinylene, piperidinylene, -imidazolidine-, -pyrrolidine-).

4.19 Compounds of Formula I-E or any of 4.1-4.17, in free or salt form, wherein Z is single bond.

4.20 Compounds of Formula I-E or any of 4.1-4.17, in free or salt form, wherein Z is a $C_1$-$C_4$alkyl.

4.21 Compounds of Formula I-E or any of 4.1-4.17, in free or salt form, wherein Z is piperidinylene or piperazinylene.

4.22 Compounds of Formula I-E or any of 4.1-4.17, in free or salt form, wherein Z is piperazinylene.

4.23 Compounds of Formula I-E or any of 4.1-4.22, in free or salt form, wherein $R_2$ is optionally substituted and saturated or unsaturated $C_1$-$C_4$ alkyl, $C_3$-$C_8$cycloalkyl optionally containing one or more heteroatoms selected from a group consisting of O or N (e.g., piperidinyl, piperazinyl, morpholinyl, imidazolinyl, pyrrolidinyl), or R$_2$ is aryl or heteroaryl optionally substituted with C$_1$-C$_4$alky, —N(R$_5$)-alkylaryl, nitro, halo or hydroxy group.

4.24 Compounds of Formula I-E or any of 4.1-4.23, in free or salt form, wherein R$_2$ is piperidinyl, piperazinyl, morpholinyl, imidazolinyl or pyrrolidinyl.

4.25 Compounds of Formula I-E or any of 4.1-4.24, in free or salt form, wherein R$_2$ is piperazinyl.

4.26 Compounds of Formula I-E or any of 4.1-4.25, in free or salt form, wherein R$_2$ is piperazin-1-yl.

4.27 Compounds of Formula I-E or any of 4.1-4.26, in free or salt form, wherein R$_3$ is H or optionally substituted and saturated or unsaturated C$_1$-C$_4$ alkyl, optionally substituted (R$_4$)(R$_5$)N—, —N(R$_4$)(R$_5$)alkyl-, aryl (e.g., phenyl, chlorophenyl, chloro-nitro-phenyl, benzylamino-nitrophenyl), heteroaryl, arylalkyl, heteroarylalkyl, or C$_3$-C$_8$cycloalkyl optionally containing one or more heteroatoms selected from a group consisting of O or N (e.g., cyclopentyl, cyclohexyl, piperazinyl, methylpiperazinyl, ethylpiperazinyl, propylpiperazinyl, piperidinyl, azepanyl, pyrrolidinyl, imidazolidinyl, methylpyrrolidinyl, ethylpyrrolidinyl, morpholinyl, tetrahydroquinolinyl);

4.28 Compounds of Formula I-E or any of 4.1-4.27, in free or salt form, wherein R$_4$ and R$_5$ are independently H, optionally substituted C$_1$-C$_4$alkyl, or R$_4$ and R$_5$ are linked together via a covalent bond so as to form a cycloalkylene containing at least one heteroatom selected from a group consisting of N and O (e.g., piperidinylene or piperazinylene), in free or salt form, useful for inhibiting platelet adhesion and aggregation.

Preferably, the compounds of the present invention is substituted thiadiazolo[3,2-a]pyrimidin-5-one in free or salt form. More preferably, the compounds of the present invention is 2-ethyl-7-(piperazin-1-yl)-5H-[1,3,4]thiadiazolo-[3,2-a]pyrimidin-5-one in free or salt form. Still more preferably, the compounds of the present invention are 7-(piperazin-1-yl)-5H-[1,3,4]thiadiazolo-[3,2-a]pyrimidin-5-ones substituted at the 2-position, e.g., with an amine which amine is linked to a carboxylic acid (—COOH) via a linker such as C$_{1-4}$alkylene (e.g., methylene, ethylene or propylene) or arylalkylene (e.g., phenylethyl), e.g., compounds of Formula I-C wherein A is S.

In another embodiment, the invention relates to pharmaceutical compositions comprising Compound of Formula I or any of Formulas I-A-I-D or 1.1-1.42, 2.1-2.18 or 3.1-3.36 as hereinbefore described, in free or pharmaceutically acceptable salt form, in combination or association with a pharmaceutically acceptable diluent or carrier, e.g., for preventing platelet adhesion and aggregation in treating thrombotic disorders in patient in need thereof (Composition I).

In another embodiment, the invention relates to Composition I as hereinbefore described wherein said Compound is compounds of Formula I-C, e.g., 2.1-2.18, in free or pharmaceutically acceptable salt form.

In another embodiment, the invention relates to pharmaceutical compositions comprising Compound of Formula I-E as hereinbefore described, in free or salt form, in combination or association with a pharmaceutically acceptable diluent or carrier, e.g., for preventing platelet adhesion and aggregation in treating thrombotic disorders in patient in need thereof (Composition I-E).

The invention further provides pharmaceutical compositions:

5.1 Composition I-E, wherein compound of Formula I-E is substituted thiadiazolo[3,2-a]pyrimidin-5-one in free or salt form;

5.2 Composition I-E, wherein compound of Formula I-E is a compound of any of formula 4.1-4.28 in free or salt form; and 5.3 Composition I-E, wherein compound of Formula I-E is 2-ethyl-7-(piperazin-1-yl)-5H-[1,3,4]thiadiazolo[3,2-a]pyrimidin-5-one in free or salt form.

In a preferred embodiment, the invention is Composition as hereinbefore described wherein said Compound is substituted thiadiazolo[3,2-a]pyrimidin-5-one in free or salt form. In an especially preferred embodiment, the invention is Composition as hereinbefore described wherein said Compound is 2-ethyl-7-(piperazin-1-yl)-5H-[1,3,4]thiadiazolo[3,2-a]pyrimidin-5-one in free or salt form. In still another preferred embodiment, the invention is Composition I as hereinbefore described wherein said Compound is Formula I-C, e.g., 2.1-2.18, in free or pharmaceutically acceptable salt form.

In another embodiment, the invention provides methods for inhibiting or reducing platelet aggregation and/or adhesion comprising administering an effective amount of a Compound of Formula I or any of Formulas I-A-I-D, 1.1-1.42, 2.1-2.18 or 3.1-3.36 as hereinbefore described, in free or salt form, such that platelet aggregation and/or adhesion is reduced (Method I).

The invention further provides for the following methods:

6.1 Method I, wherein compound of Formula I or any of I-A-I-D is Compounds of Formula I-C or 2.1-2.18, in free or salt form.

6.2 Method I or 6.1, wherein reduction of platelet aggregation and/or adhesion treats or inhibits a thrombotic disorder, e.g. is selected from a group consisting of stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.

In another embodiment, the invention provides methods for inhibiting or reducing platelet aggregation and/or adhesion comprising administering an effective amount of Compound of Formula I-E or any of 4.1-4.28, in free or salt form, such that platelet aggregation and/or adhesion is reduced (Method I-E).

The invention further provides for the following methods:

6.3 Method I-E, wherein compound of Formula I-E is substituted thiadiazolo[3,2-a]pyrimidin-5-one in free or salt form.

6.4 Method I-E or 6.3, wherein Compound of Formula I-E is 2-ethyl-7-(piperazin-1-yl)-5H-[1,3,4]thiadiazolo[3,2-a]pyrimidin-5-one in free or salt form.

6.5 Method I-E or 6.3 or 6.4, wherein reduction of platelet aggregation and/or adhesion treats or inhibits a thrombotic disorder, e.g. is selected from a group consisting of stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.

In a preferred embodiment, the invention is Method I wherein said compound is Compounds of Formula I-C or 2.1-2.18, in free or salt form. In yet another preferred embodiment, the invention is Method I-E wherein said compound is substituted thiadiazolo[3,2-a]pyrimidin-5-one in free or salt form. In an especially preferred embodiment, the invention is Method I or I-E wherein said compound is 2-ethyl-7-(piperazin-1-yl)-5H-[1,3,4]thiadiazolo[3,2-a]pyrimidin-5-one in free or salt form.

In yet another embodiment, the invention provides methods for inhibiting or reducing both platelet aggregation and adhesion comprising administering an effective amount of Compound of Formula I or any of, I-A-I-E, or 1.1-1.42, 2.1-2.18, 3.1-3.36 or 4.1-4.28 in free or salt form, such that both platelet aggregation and adhesion are reduced (Method I').

In another embodiment, the invention provides methods for the treatment or prophylaxis of a thrombotic disorder comprising administering to a subject at risk of thrombotic disorder an effective amount of a compound of Formula I or any of Formulas I-A-I-D or 1.1-1.42, 2.1-2.18, or 3.1-3.36, in free or pharmaceutically acceptable salt thereof, such that platelet aggregation or adhesion is reduced (Method II).

The invention further provides for the following methods:
7.1 Method II, wherein said thrombotic disorder is selected from a group consisting of stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.
7.2 Method II or 7.1, wherein said thrombotic disorders is thrombosis as a result of angioplasty or stent placement.
7.3 Method II, 7.1 or 7.2, wherein subject at risk of thrombotic disorder is a subject who has a history of vascular surgery.
7.4 Method II or any of Methods 7.1-7.3, wherein said compound is compound of Formula I or any of I-A-I-D or 1.1-1.42, 2.1-2.18, or 3.1-3.36, in free or pharmaceutically acceptable salt form.
7.5 Method II or any of Methods 7.1-7.4, further comprises administering an effective amount of at least one therapeutic agent selected from a group consisting of anti-coagulant, antiplatelet, and thrombolytic agents in conjunction with a compound of Formula I or any of Formulas I-A-I-D or 1.1-1.42, 2.1-2.18, or 3.1-3.36, in free or pharmaceutically acceptable salt thereof.
7.6 Method II, or any of Methods 7.1-7.5, further comprises administering an effective amount of at least one therapeutic agent selected from a group consisting of heparin, low molecular weight heparins, bivalirudin, Fondaparinux, warfarin, Acenocoumarol, Phenprocoumon, Phenindione, Abbokinase (urokinase), streptokinase, alteplase, retaplase, tenecteplase, prasugrel, prasugrel, aspirin, ticlopidine, clopidogrel, abciximab, eptifibatide and tirofiban in conjunction with Compound of Formula I or any of Formulas I-A-I-D or 1.1-1.42, 2.1-2.18, or 3.1-3.36, in free or pharmaceutically acceptable salt thereof.
7.7 Method II or any of Methods 7.1-7.5, further comprises administering anticoagulant or thrombolytic agents in conjunction with Compound of Formula II-A-I-D or 1.1-1.42, 2.1-2.18, or 3.1-3.36, in free or pharmaceutically acceptable salt thereof.
7.8 Method II or any of Methods 7.1-7.5, further comprises administering heparin in conjunction with Compound of Formula II-A-I-D or 1.1-1.42, 2.1-2.18, or 3.1-3.36, in free or pharmaceutically acceptable salt thereof.

In another embodiment, the invention provides methods for the treatment or prophylaxis of a thrombotic disorder comprising administering to a subject at risk of thrombotic disorder an effective amount of Compound of Formula I-E or 4.1-4.28 or pharmaceutically acceptable salt thereof such that platelet aggregation or adhesion is reduced (Method II-E).

The invention further provides for the following methods:
7.9 Method II-E, wherein said thrombotic disorder is selected from a group consisting of stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.
7.10 Method II-E or 7.9, wherein said thrombotic disorders is thrombosis as a result of angioplasty or stent placement.
7.11 Method II-E, 7.9 or 7.10, wherein subject at risk of thrombotic disorder is a subject who has a history of vascular surgery.
7.12 Method II-E or any of Methods 7.9-7.11 wherein Compound of Formula I-E is any of compounds of formula 4.1-4.28.
7.13 Method II-E or any of Methods 7.9-7.11, wherein Compound of Formula I-E is substituted thiadiazolo[3,2-a]pyrimidin-5-one in free or salt form.
7.14 Method II-E or any of Methods 7.9-7.11, wherein Compound of Formula I-E is 2-ethyl-7-(piperazin-1-yl)-5H-[1,3,4]thiadiazolo[3,2-a]pyrimidin-5-one in free or salt form.
7.15 Method II-E or any of Methods 7.9-7.14, further comprises administering an effective amount of at least one therapeutic agent selected from a group consisting of anti-coagulant, antiplatelet or thrombolytic agents in conjunction with Compound of Formula I-E or any of compound of formula 4.1-4.28 or pharmaceutically acceptable salt thereof.
7.16 Method II-E or any of Methods 7.9-7.15, further comprises administering at least one therapeutic agent selected from a group consisting of heparin, low molecular weight heparins, bivalirudin, Fondaparinux, warfarin, Acenocoumarol, Phenprocoumon, Phenindione, Abbokinase (urokinase), streptokinase, alteplase, retaplase, tenecteplase, prasugrel, aspirin, ticlopidine, clopidogrel, abciximab, eptifibatide and tirofiban in conjunction with Compound of Formula I-E or any of compound of formulas 4.1-4.28 or pharmaceutically acceptable salt thereof
7.17 Method II-E or any of Methods 7.9-7.15, further comprises administering heparin in conjunction with Compound of Formula I-E or any of compound of formula 4.1-4.28 or pharmaceutically acceptable salt thereof.

In a preferred embodiment, the invention is a method of treating a thrombotic disorder comprising administering an effective amount of substituted thiadiazolo[3,2-a]pyrimidin-5-one in free or salt form. In an especially preferred embodiment, the invention is a method of treating a thrombotic disorder comprising administering an effective amount of 2-ethyl-7-(piperazin-1-yl)-5H-[1,3,4]thiadiazolo[3,2-a]pyrimidin-5-one in free or salt form. In yet another preferred embodiment, the invention is a method of treating a thrombotic disorder comprising administering heparin in conjunction with an effective amount of 2-ethyl-7-(piperazin-1-yl)-5H-[1,3,4]thiadiazolo[3,2-a]pyrimidin-5-one in free or salt form. In yet another preferred embodiment, the invention is a method of treating a thrombotic disorder comprising administering an effective amount of Compounds of Formula I-C or 2.1-2.18 in free or pharmaceutically acceptable salt form.

The invention further provides any of the foregoing methods wherein the compounds of the present invention reduce platelet aggregation and/or adhesion, e.g., with an $IC_{50}$ of less than 50 µM, preferably less than 25 and most preferably less than 1 µM in an ADP or other agonist-induced platelet aggregation assay and/or in a fibrinogen binding assay as described in the examples below.

In yet another embodiment, the invention provides a method (Method IIIa) for screening for platelet inhibitor compounds comprising screening for test compounds for (i) inhibition of platelet adhesion to fibrinogen and (ii) for inhibition of platelet aggregation, wherein compounds are selected on the basis of their ability to inhibit both platelet adhesion and platelet aggregation, e.g., with an $IC_{50}$ of less than 100 µM, preferably less than 1 µM, and most preferably less than 0.01 µM in an ADP or other agonist-induced platelet aggregation assay and/or in a fibrinogen binding assay as described in the examples below.

In yet another embodiment, the invention provides methods for identifying candidate platelet inhibitors binding to αIIbβ3 (Method Mb) comprising:
i) incubating cells expressing αIIbβ3 in the presence or absence of a test compound and in the presence or absence of one or more agents known to bind to and directly activate αIIbβ3 so as to expose β3 LIBS, (e.g., tirofiban, eptifibatide);
ii) assaying binding of one or more LIBS-specific mAbs to αIIbβ3 (e.g., one or more of APS, PMI-1 or LIBS-1); and
iii) evaluating the ability of a test compound to affect binding of the LIBS-specific mAbs to αIIbβ3.

Without being bound to any theory, it is believed that binding of ligand by the receptor induces conformational changes in αIIbβ3, exposing the ligand-induced binding sites (LIBS). With traditional αIIbβ3-inhibitors such as tirofiban and eptifibatide, binding to the αIIbβ3 integrin's extracellular structure inhibits platelet adhesion. However, upon dissociation of these ligands, the integrin is thought to remain in its high affinity conformation, capable of binding circulating soluble fibrinogen, thus increasing the risk for thrombotic complications following αIIbβ3 inhibitor therapy. The present invention identifies αIIbβ3 inhibitors that are capable of inhibiting fibrinogen binding without inducing β3 LIBS exposure in a high affinity conformation. For example, in one embodiment, compounds of the invention may bind to αIIb, and in some cases induce αIIb LIBS exposure, without inducing β3 LIBS exposure. Thus the compounds may expose LIBS of the αIIb subunit without exposing LIBS of the β3 subunit, so that the receptor is not in a high affinity conformation. Such compounds thus demonstrate specific binding to αIIbβ3 integrin and inhibition of platelet adhesion without the disadvantage of inducing the high affinity conformation of the αIIbβ3 and consequent risk of complications following dissociation of the compounds from the αIIbβ3.

The invention thus further provides the following methods:
8.1 Method IIIa or IIIb, wherein a useful platelet inhibitor is a compound that (i) binds αIIb and optionally may increase binding of at least one αIIb LIBS-specific mAb relative to binding to unactivated platelets; and (ii) does not increase binding of one or more β3 LIBS-specific mAbs relative to binding to unactivated platelets and/or reduces binding relative to binding in the presence of an agent known to bind to and directly activate αIIbβ3 so as to expose LIBS.
8.2 Method 8.1, wherein the one or more αIIb LIBS-specific mAbs comprise PMI-1.
8.3 Method 8.1 or 8.2, wherein the one or more β3 LIBS specific mAbs comprise LIBS-1 and/or APS.
8.4 Method IIIb, 8.1 8.2 or 8.3, wherein said LIBS-specific mAbs are labeled.
8.5 Method 8.4, wherein said LIBS-specific mAbs are fluorescently labeled.

The invention thus provides a αIIbβ3-binding compound (a Platelet Inhibitor of the Invention) which (i) inhibits platelet adhesion to fibrinogen and (ii) inhibits platelet aggregation; for example, a compound which (i) binds αIIb and optionally may increase binding of at least one αIIb LIBS-specific mAb relative to binding to unactivated platelets; and (ii) does not increase binding of one or more β3 LIBS-specific mAbs relative to binding to unactivated platelets and/or reduces binding relative to binding in the presence of an agent known to bind to and directly activate αIIbβ3 so as to expose LIBS. For example, the invention provides a compound identified according to any of Methods IIIa, IIIb or 8.1-8.5. Compound of Formula I or any of Formulas I-A-I-E or 1.1-1.42, 2.1-2.18, 3.1-3.36 or 4.1-4.28, in free or salt form, for use in the present invention, are preferably compounds which are active in any of Methods IIIa, IIIb or 8.1-8.5, e.g., which bind to αIIbβ3 without presenting β3 LIBS in a high affinity conformation, e.g., as determined in accordance with Method IIIa or IIIb, e.g., any of methods 8.1-8.5.

In another embodiment, the invention provides a drug-eluting stent wherein the drug or drugs eluted comprise a Platelet Inhibitor of the Invention, or a Compound of Formula I or any of Formulas I-A-I-D or 1.1-1.42, 2.1-2.18, 3.1-3.36. For example, the invention provides a stent, e.g., an arterial stent, for example a coronary artery or carotid artery stent, which comprises a biocompatible polymer matrix which comprises or is associated with a Compound of or any of Formulas I-A-I-D or 1.1-1.42, 2.1-2.18, 3.1-3.36., in free or salt form. The stent may be made of metal, plastic, biodegradable or bioabsorbable material or combination thereof, e.g., stainless steel, nickel-titanium alloy, colbalt-alloy, tantalum, silicone, polytetrafluoroethylene, magnesium alloy or poly-L-lactide. For example, a stent may be a metallic stent (e.g., stainless steel, nickel-titanium alloy, colbalt alloy, or tantalum) partially or wholly coated with a biocompatible polymer, e.g., a plastic (e.g., polytetrafluoroethylene) or a polymeric carrier (e.g., phosphorylcholine or polylactic acid) which polymer comprises or is associated with a Compound of or any of Formulas I-A-I-D or 1.1-1.42, 2.1-2.18, 3.1-3.36. e.g., such that said Compound is presented or released in a manner and amount effective to inhibit platelet adhesion and/or aggregation in the vicinity of the stent. The stent may further comprise or be associated with an additional drug or drugs, e.g., an antiproliferative agent, e.g., sirolimus, everolimus, zotarolimus, tacrolimus, or paclitaxel, and/or an anticoagulant, e.g., heparin.

In yet another embodiment, the invention provides a drug-eluting stent as hereinbefore described wherein the drug or drugs eluted comprise a Compound of Formula I-E, e.g., of 4.1-4.28.

In another embodiment, the invention provides a Compound of Formula I or any of Formulas I-A-I-D or 1.1-1.42, 2.1-2.18, 3.1-3.36, in free or salt form, for use as a pharmaceutical, e.g. for use of a Compound of Formula I or any of Formulas I-A-I-D or 1.1-1.42, 2.1-2.18, 3.1-3.36, in the manufacture of a medicament for treatment or prophylaxis of a thrombotic disorder, e.g., according to any of Method II or any of methods 7.1-7.8.

In yet another embodiment, the invention provides a Compound of Formula I-E or any of 4.1-4.28, in free or salt form, for use as a pharmaceutical, e.g. use of a Compound of Formula I-E or any of 4.1-4.28 in the manufacture of a medicament for treatment or prophylaxis of a thrombotic disorder, e.g., according to any of Method II-E or any of methods 7.9-7.17. The invention also provides uses as hereinbefore described, wherein Compound of Formula I or any of Formulas I-A-I-D or 1.1-1.42, 2.1-2.18, 3.1-3.36 is compound of Formula I-C in free or pharmaceutically acceptable salt form. The invention further provides uses as hereinbefore described, wherein Compound of Formula I-E is substituted thiadiazolo[3,2-a]pyrimidin-5-one in free or salt form, preferably, 2-ethyl-7-(piperazin-1-yl)-5H-[1,3,4]thiadiazolo[3,2-a]pyrimidin-5-one in free or salt form.

DETAILED DESCRIPTION OF THE INVENTION

The numbering of thiadiazolo[3,2-a]pyrimidin-5-ones and oxadiazolo[3,2-a]pyrimidin-5-ones as described herein is shown as an example:

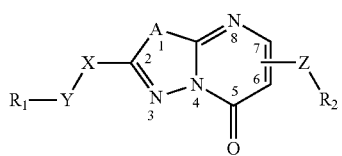

Formula I wherein A is S or O.

The numbering of triazolo[1,5-a]pyrimidin-7-ones and pyrazolo[1,5-a]pyrimidin-7-ones as described herein is shown as an example:

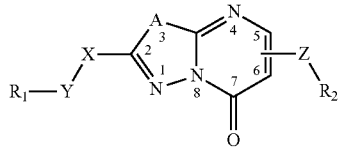

Formula I wherein A is C or N.

As used herein, the term "αIIbβ3" or "integrin WIND" refers to the receptor on the surface of human platelets. It is a heterodimeric complex composed of both αIIb and β3 subunits responsible for binding adhesive plasma proteins, most notably fibrinogen and von Willebrand factor.

The term "antagonist" refers to any ligand or molecule that binds to receptors and competitively or noncompetitively blocks the binding of ligand to that receptor. Therefore, "αIIbβ3 antagonist" refers to any ligand or molecule that competitively or noncompetitively blocks αIIbβ3.

"LIBS" refers to ligand-induced binding sites on αIIbβ3 that are presented or exposed upon the binding of a ligand or antagonist by the receptor.

"LIBS-specific mAbs" refers to monoclonal antibodies that bind to the exposed ligand-induced binding sites of αIIbβ3. Examples of LIBS-specific mAbs include APS, PMI-1 and LIBS1.

The term "thrombotic disorders" refers to disorders characterized by formation of a thrombus that obstructs vascular blood flow. Examples of thrombotic disorders include stroke, myocardial infarction, stable or unstable angina, peripheral vascular disease, abrupt closure following angioplasty or stent placement and thrombosis induced by vascular surgery. Thrombotic disorders also include disorders characterized by formation of a thrombus caused by atrial fibrillation or inflammation.

The phrase "subject at risk of thrombotic disorders" or "subject in need thereof" includes subjects who have a history of vascular intervention (e.g. angioplasty, stent placement, aortocoronary bypass or insertion of prosthetic heart valves), cardiovascular abnormality (e.g. atrial fibrillation) or a family history of vascular diseases (e.g., coronary artery disease (CAD), systemic hypertension, diabetes mellitus, hyperlipidemia, bicuspid aortic valve, hypertrophic cardiomyopathy or mitral valve prolapse).

The term "platelet adhesion" refers to the binding of platelet membrane proteins to fibrinogen, collagen, von Willebrand factor (vWF) or other adhesive glycoproteins (e.g., fibronectin, laminin).

The term "platelet aggregation" refers to the attachment of activated platelets one to another, which results in the formation of aggregates or clumps of activated platelets.

The phrase "inhibit or reduce platelet adhesion or aggregation" is intended to mean at least a 50% inhibition of platelet activity at a concentration of 100 μM or lower in a given assay, relative to platelet activity in the absence of the compound.

The phrase "antagonist known to expose LIBS" herein refers to agents that bind to and directly activate αIIbβ3, for example tirofiban and eptifibatide.

The term "anticoagulants" herein refers to any compound or substance that either stimulates natural inhibitor of coagulant proteases or blocks the coagulation cascade. Examples of anticoagulants include, but are not limited to heparin, warfarin, phenprocoumon, fondaparinux, lepirudin, bivalirudin, argatroban, danaparoid and drotrecogin alfa.

The term "anti-platelet agents" herein refers to compound or substance that prevents platelet adhesion or aggregation. Examples of anti-platelet agents include, but are not limited to prasugrel, aspirin, ticlopidine, clopidogrel, abciximab, eptifibatide and tirofiban.

The term "fibrinolytic agents" therefore refers to any compound or substance that lyses pathological thrombi. "Thrombolytic agents" are agents that are fibrinolytic, i.e., agents that convert plasminogen to plasmin, which lyses fibrin. Examples of fibrinolytic agents include but are not limited to streptokinase and tissue plasminogen activator (t-PA).

The term "stent" herein refers to expandable wire form or perforated tube that is inserted into a natural conduit of the body, such as an artery, usually a coronary artery, to prevent or counteract a disease-induced localized flow constriction.

The binding of LIBS-specific mAbs to αIIbβ3 may be measured by comparing the binding of LIBS-specific mAbs to αIIbβ3 in the presence of testing compound with the binding of LIBS-specific mAbs to αIIbβ3 in the absence or presence of a control such as untreated platelets and/or other known αIIbβ3 inhibitors that are known to cause β3 LIBS exposure, e.g., tirofiban or epifibatide. For example, the test compound may bind to αIIb and optionally increases binding of at least one αIIb LIBS-specific mAb relative to binding to unactivated platelets without increasing the binding of one or more β3 LIBS-specific mAbs relative to binding to unactivated platelets and/or reduces binding relative to binding in the presence of an agent known to bind to and directly activate αIIbβ3 so as to expose LIBS.

It is understood that the term "substituted with" means substitution that is in accordance with permitted valence of the substituted atom and the substituent, and that the substitution results in a stable compound. The term "substituted" is contemplated to include all permissible substituent of organic compounds. Permissible substituents include halogen, hydroxyl, carbonyl, thiocarbonyl, alkoxyl, amino, amido, imine, cyano, nitro, sulhydryl, sulfate, sulfonate, sulfonyl as well as acyclic and cyclic, branched and unbranched, carbocyclic and heterocyclic, aromatic and nonaromatic substitutents of organic compounds. Permissible substitutent also include —COOH.

As used herein, the term "alkyl" or "alkyl chain" or "alkylene" refers to a linear or branched, aliphatic hydrocarbon.

The term "alkenyl" or "alkenylene" refers to unsaturated aliphatic groups such as an alkyl group containing at least one double bond. Examples of alkenyl include, but are not limited to, ethenyl, propenyl, butenyl, pentenyl, hexenyl, 2-methyl-2-propenyl, 4-methyl-3-pentenyl, and the like. The term "alkynyl" or "alkynylene" refers to unsaturated aliphatic groups such as an alkyl group containing at least one triple bond.

The term "$C_3$-$C_{10}$cycloalky" refers to saturated, carbocyclic, hydrocarbon radicals having three to eight carbon atoms. Examples of $C_3$-$C_{10}$cycloalkyl optionally containing one or more heteroatoms selected from a group consisting of O or N include, but are not limited to, cyclopropyl, cyclobutyl, cyclopentyl, cyclopentenyl, cyclohexyl or cyclohexenyl, piperidinyl, piperazinyl, morpholinyl, imidazolinyl, pyrrolidinyl. These cycloalkyl systems may be attached via the heteroatom or any other carbon on the system. $C_3$-$C_{10}$cycloalky may also refer to non-aromatic cyclic system fused to an aromatic cyclic system. An example of this includes tetrahydroquinolinyl.

The term "aryl" refers to any ring system having a 4n+2 Pi electrons within the ring system, wherein n is an integer. Aromatic compounds include phenyl, naphthyl and their derivatives.

The term "heteroaryl" is intended to mean a stable 5- to 6-membered monocyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring.

The term "amido" refers to —C(O)N— or —NC(O)—.

Compounds of the Invention may exist in free or salt form, e.g., as acid addition salts. In this specification unless otherwise indicated language such as Compounds of the Invention is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the present invention may be administered orally or parenterally, including intravenous, intramuscular, intraperitoneal, subcutaneous, transdermal, airway (aerosol), rectal, vaginal and topical (including buccal and sublingual) administration. The compounds useful in the invention may generally be provided in the form of tablets or capsules, as a powder or granules, or as an aqueous solution or suspension. Tablets for oral use may include the active ingredients mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Dosages of the compounds of the invention will vary depending upon the condition to be treated or prevented and on the identity of the inhibitor being used. Estimates of effective dosages and in vivo half-lives for the individual compounds encompassed by the invention can be made on the basis of in vivo testing using an animal model, such as the mouse model described herein or an adaptation of such method to larger mammals. Appropriate dosage may range from 0.01 mg to 500 mg.

In addition to their administration singly, the compounds useful according to the invention can be administered in combination or in conjunction with other known therapeutic agents useful for thrombotic disorders such as anticoagulants (e.g., heparin, warfarin, phenprocoumon, fondaparinux, lepirudin, bivalirudin, argatroban, danaparoid, drotrecogin alfa), fibrinolytic agents (e.g., streptokinase or tissue plasminogen activator (t-PA) or other anti-platelet agents (e.g., prasugrel, aspirin, ticlopidine, clopidogrel, abciximab, eptifibatide and tirofiban). In any event, the administering physician can adjust the amount and timing of drug administration on the basis of results observed using standard measures of platelet activity known in the art or described herein.

EXAMPLES

Synthesis of Compounds of the present invention. The compounds described herein and their pharmaceutically acceptable salts may be made using the methods as described and exemplified herein and by methods similar thereto and by methods known in the chemical art. In the description of the synthetic methods described herein, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Therefore, at times, reaction may require to be run at elevated temperature, for a longer or shorter period of time or in the presence of an acid or base. It is understood by one skilled in the art of organic synthesis that functionality present on various portions of the molecule must be compatible with the reagents and reactions proposed. If not commercially available, starting materials for these processes may be made by procedures, which are selected from the chemical art using techniques similar or analogous to the synthesis of known compounds. All references cited herein are hereby incorporated in their entirety by reference.

The compounds of the present invention may be made, e.g., by first preparing Compound B by the addition of oxopropanoate to Compound A (e.g., 1,3,4-thiadiazol-2-amine, 1,3,4-oxadiazol-2-amine, 4-H-pyrazol-3-amine or 4-H-1,2,4-triazol-3-amine) as demonstrated in Scheme-1 below wherein all substituents are as previously defined, followed by cyclization in the presence of $POCl_3$ and coupling of $R_2$—Z, e.g., $R_2$-piperazine, $R_2$-piperidine, piperazine, piperidine, or morpholine, to the product of the cyclization step. $R_1$—Y—X may then be attached to Compound B by first halogenating it, e.g., brominating it in the presence of sodium acetate and acetic acid to obtain Compound C, followed by coupling of Compound C with $R_1$—Y—X, e.g., phenyl$C_{1-4}$ alkylamine optionally substituted with —COOH, e.g., benzylamine, phenylethylamine, or 4-(2-aminoethyl)-benzoic acid. Coupling of $R_1$—Y—X with Compound C may be carried out in the presence of a base such as triethylamine or diisopropyl ethyl amine in a solvent such as ethanol or dimethylformamide, e.g., at 90-150° C.

Scheme-1

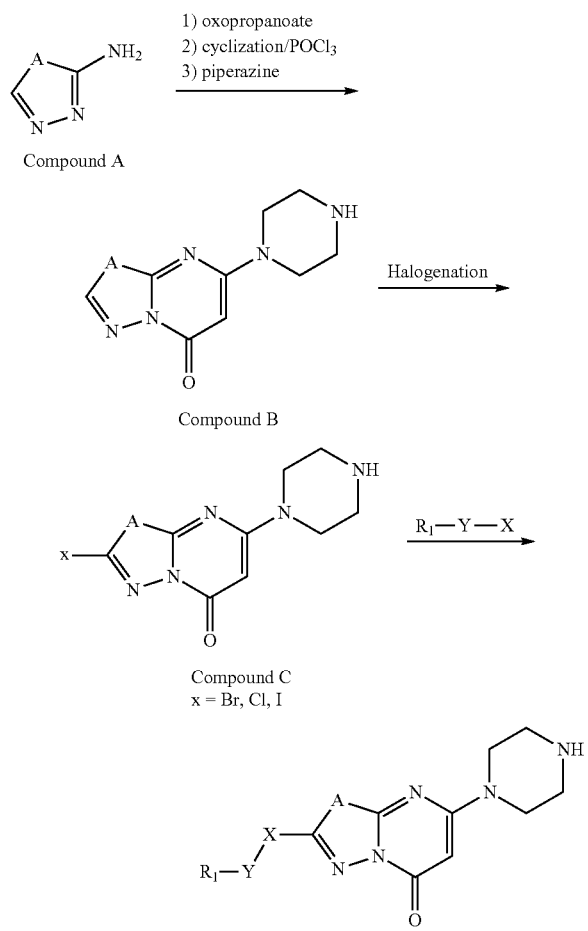

Alternatively, the compounds may be made by the following steps: (1) halogenating e.g., brominating Compound A; (2) protecting Compound D (e.g., with BOC anhydride); (3) coupling of R₁—Y—X with Compound E; (4) deprotecting Compound F, e.g., with an acid (e.g., triflouroacetic acid); (5) adding oxopropanoate; (6) cyclizing in the presence of POCl₃ and 7) coupling the product with piperazine.

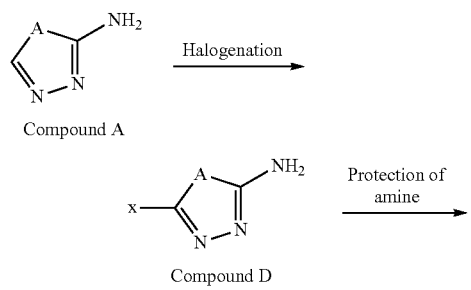

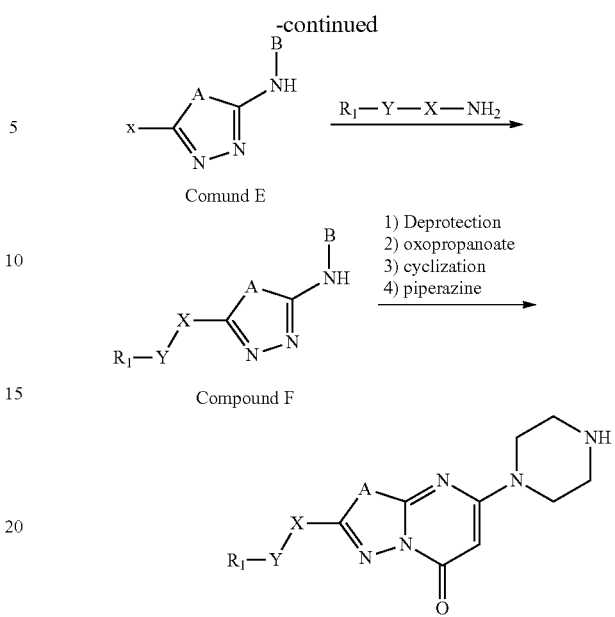

Thiadiazolo[3,2-a]pyrimidin-5-one derivatives may also be synthesized by treating heteroarylamines (e.g., 2-Amino-1,3,4-thiadiazole, 2-Amino-5-methyl-1,3,4-thiadiazole, 2-Amino-5-ethyl-1,3,4-thiadiazole) with diaryl malonate (e.g. di(2,4,6-trichlorophenyl)malonate) at 180° C. or with ethyl-3-chloro-3-oxopropanoate at 60° C. in the presence of pyridine. The resulting compound may then be heated in excess phosphorus oxychloride at 120° C. to yield 7-chloro-thiadiazolo[3,2-a]pyrimidin-5-one core (e.g., 7-chloro-thiadiazolo[3,2-a]pyrimidin-5-one, 7-chloro-2-ethyl-5H-[1,3,4]thiadiazolo[3,2-a]pyrimidin-5-one or 7-chloro-2-methyl-5H-[1,3,4]thiadiazolo[3,2-a]pyrimidin-5-one). Derivative groups may be attached onto the 7-position of the core structure by treating the resulting chloro-thiadiazolo[3,2-a]pyrimidin-5-one core with excess cyclic amines (e.g. piperazine, piperidine, pyrrolidine, imidazolidine) in refluxing ethanol. Further derivatives on the piperazine may be made by treating the cyclic amine thiadiazolo[3,2-a]pyrimidin-5-one derivatives with aryl halides (e.g., 1,4-dichloro-2-nitrobenzene).

Platelet Preparation for Primary Screen. Day-old platelet concentrate is obtained from the New York Blood Center as a ~50 ml suspension of platelets in citrated plasma containing between $1.5 \times 10^6$ and $3.0 \times 10^6$ platelets/μl. Platelet count is determined with an automated dual angle laser particle counter (Bayer ADVIA 120), and platelets are separated into 5 ml aliquots, to which 5 ml HEPES modified Tyrode's buffer (HBMT) pH 7.4 (138 mM NaCl, 12 mM NaHCO3, 10 mM HEPES, 2.7 mM KCl, 0.4 mM NaH2PO4, 0.1% glucose, 0.35% BSA) is added along with $PGE_1$ (1 μM). Tubes are centrifuged at 1200 g for 8 min at room temperature, and resuspended in 1 ml HBMT. Platelets are labeled with 7 μM calcein-acetoxymethyl ester (Invitrogen) for 30 min at room temperature in the dark. Tubes are then filled to 10 ml with HBMT, treated with $PGE_1$ (1 μM), and centrifuged 8 min at 1200 g to remove unincorporated dye. Platelet pellets are resuspended in 2 ml HBMT containing 2 mM CaCl₂, 1 mM MgCl₂. Platelet count is adjusted to 500,000/μl.

Platelet Adhesion Assay. Human fibrinogen (American Diagnostica) is prepared as a 50 μg/ml solution in Tris/Saline pH 7.4 (50 mM Tris, 100 mM NaCl). Black-walled, clear-bottomed, polystyrene 384 well untreated, non-sterile plates (Corning #3711) are used in the assay. Fibrinogen solution is added to plates in 30 μl aliquots per well using a WellMate peristaltic microplate dispenser (Matrix) and plates are incubated at room temperature for 1 hr. Plates are washed 4 times with Tris/Saline using an ELX405 automated plate washer (Bio-Tek) and blocked with HBMT containing 0.35% BSA for no less than 1 hr. Blocked, fibrinogen-coated plates are washed with HBMT+BSA two times. A final aspiration is performed on the plates following their second wash, such that 15 μl of buffer remained in each well. Addition of compounds is performed using a MiniTrak V liquid handling robot (PerkinElmer), which dispenses a 0.1 μl aliquot of 5 mM solutions of compound in DMSO, (16.6 μM final in 30 μl after addition of platelets). Aliquots of 15 μl calcein-labeled platelets are then added, resulting in a final count of 250,000/μl in 30 μl. After 1 hr of incubation with platelets, a final wash is performed on plates using 4 wash/rinse cycles with HBMT containing BSA and ions, leaving 50 μl of buffer in each well. Positive controls consist of wells containing platets without Compounds. Negative controls are wells containing platelets and known inhibitors of αIIbβ3, including mAbs 7E3 and 10E5, and EDTA. The relative number of adherent platelets is measured by assessing the fluoroesence of the labeled platelets by exciting wells with 490 nm light and reading at 515 nm using a Fusion automated plate reader (PerkinElmer).

Platelet Preparation from Peripheral Blood. After informed consent is obtained from healthy human donors who have not taken any medication known to inhibit platelet function for at least 7 days, peripheral venous blood is collected via a 19-gauge butterfly needle into tubes containing either a 10% volume of sodium citrate (3.8%), or a 15% volume of Acid-Citrate-Dextrose (ACD-A, 74.8 mM sodium citrate, 38 mM citric acid, 124 mM dextrose). Platelet-rich plasma (PRP) is prepared by centrifugation at 650 g for 4 minutes at 22° C. and is gently removed with a plastic pipette. Platelet-poor plasma (PPP) is prepared by further centrifugation of the remaining blood at 3000 g for 10 minutes at 22° C. Washed platelets (WP) are prepared by treating ACD-anticoagulated PRP with 1 μM $PGE_1$, adding 0.10 vol ACD, and centrifuge at 1200 g for 8 min at 22° C. The platelet pellet is resuspended in HBMT. Platelet counts are determined with the automated particle counter (ADVIA 120 hematological analyzer Bayer).

Platelet Aggregation in 96-well Plates. Untreated 96-well polystyrene plates (Nunc) are blocked for at least 1 hour with HBMT containing BSA. Compounds are added to blocked wells containing 50 μl HBMT as 0.5 μl of 5 mM solutions in DMSO. A 16.6 μl sample is removed from each well prior to addition of PRP, such that the final concentration of compounds after addition of platelets is 16.6 μM. A 66.6 μl sample of citrated PRP from volunteer blood donors is added to compound-containing wells, and plates are allowed to equilibrate to 37° C. in the plate reader (SpectraMax) for 10 minutes. Aggregation is induced via addition of ADP (5 μM final conc.). Absorbance is measured at 563 nm every 10 seconds with shaking for 3 s between reads for 8 minutes. Percent aggregation is calculated as $(Abs_{PRP}-Abs_{sample})/(Abs_{PRP}-Abs_{PPP})$.

Platelet Aggregation in Aggregometer. Citrated PRP is incubated with compounds or controls for 15 min 37° C. in 300-500 μl vols in glass aggregometer tubes. Agonists are added after 30 s equilibration in the aggregometer (Kowa) and light transmittance is measured for 8 min. Agonists include ADP, collagen (native type 1 collagen fibrils), restocetin, arachidonic acid, and thrombin receptor activating peptide [TRAP (SFLLRN)].

mAb Binding. PRP anticoagulated with ACD is centrifuged at 1200 g for 8 min and is resuspended in HBMT containing 2 mM $Ca^{2+}$, 1 mM $Mg^{2+}$. Platelet count is adjusted to 250,000/μl. Platelets are incubated with the Compounds (100 μM), tirofiban (100 μM), EDTA (10 mM), or 10E5 (10 μg/ml) for 15 min, at 37° C. Samples are incubated with Fluorescently-labeled monoclonal antibodies (PMI-1, LIBS-1, AP5, 7H2, 7E3, or 10E5; Alexa-488-conjugated, Invitrogen) at 20 μl, 5 μg/ml final concentration for 30 min at room temperature in the dark before diluting 1:10 for analysis on a FACSCalibur flow cytometer (Becton Dickson). Antibody binding is reported as the geometric mean fluorescence intensity; nonspecific binding is determined by adding a 50-fold excess of unlabeled antibody before adding labeled antibody.

Fluorescent Fibrinogen Binding. Washed platelets at 250,000/μl or αIIbβ3-expressing HEK293 cells at $10 \times 10^6$/ml in HBMT with 2 mM $Ca^{2+}$/1 mM $Mg^{2+}$ are incubated with compounds or controls and 200 μg/ml fluorescent fibrinogen (Invitrogen) with or without 60 μg/ml of the activating mAb AP5 for 30 min at 22° C. in the dark. Unbound fibrinogen is removed by centrifugation at 1800 rpm for 3 min and the platelets are resuspended in HBMT before FACS analysis.

Platelet and Cell Adhesion. Platelets are prepared from ACD-anticoagulated blood as previously described. Cells, either CS1 (αVβ3-expressing) or HEK293 (αIIbβ3-expressing) are separated from culture media by centrifugation at 200 g, 4 min. Cells are resuspended in HBMT containing 1 mM $MgCl_2$ (CS1 cells) and/or 2 mM $CaCl_2$ (HEK293 cells). Polystyrene 96-well microtiter plates (Nunc) are coated with either fibrinogen (50 μg/ml), vitronectin (5 μg/ml), or collagen (33 μg/ml, rat tail type 1, Becton Dickson) for 1 h, and blocked with HBMT for at least 1 h. Platelets and cells are treated with compounds or control solutions for 15 min at 37° C. before they are added to the microtiter wells. After adhering for 1 h at either 22° C. (platelets) or 37° C. (cells), non-adherent platelets or cells are removed by washing 3 times with HBMT containing the same ion composition as the buffer used for adhesion. Adherent platelets or cells are quantified by their endogenous acid phosphatase activity on p-nitrophenyl phosphate (pNPP) (1 mg/ml in 0.1 M sodium citrate, 0.1% Triton X-100, pH 5.4). In other experiments, 8-chambered glass coverslips (Nunc) are coated with collagen (33 μg/ml) for 1 h at 22° C. Washed platelets are allowed to adhere for 1 h at 22° C. and the coverslips are stained with the Alexa-488-conjugated β3-specific mAb 7H2. Adherent platelets are imaged using a Zeiss LSM-510 confocal system with Axiovert 200 microscope (Carl Zeiss, Germany) using a Plan-Apochromat 100×/1.4 NA oil DIC objective.

Fibrinogen Binding to Purified αIIbβ3. The anti-β3 mAb 7H2 (10 μg/ml) is adsorbed to polystyrene microtiter plate wells overnight at 4° C., and wells are then blocked with 3.5% BSA for 1 h at 22° C. Purified αIIbβ3 (Enzyme Research Laboratories, South Bend, Ind.) is diluted in buffer A (50 mM Tris/HCl, 100 mM NaCl, 1 mM $CaCl_2$, 1 mM $MgCl_2$, 1% BSA, 0.0035% Triton X-100) to 10 μg/ml, and is allowed to adhere to wells coated with mAb 7H2 for 2 h at 37° C. Wells are then washed 3 times with buffer A. Fibrinogen, prepared in buffer A (20 μg/ml) in the presence or absence of mAb AP5 (60 μg/ml), is incubated in plate wells for 2 h at 37° C. with or without the Compounds or control solutions. Wells are washed 3 times with buffer A and then incubated with a horseradish peroxidase-conjugated polyclonal anti-fibrinogen antibody (1:1,000 in buffer A; DAKO, Glostrup, Denmark) for 1 h at 22° C. Wells are washed 3 times, 200 μl of a peroxidase substrate [3,3',5,5'-tetramethylbenzidine (TMB), Sigma-Aldrich] is added, the reaction is terminated after 30 min by acidification with 50 μl 0.5 M $H_2SO_4$, and absorbance is determined at 450 nm. For priming experiments the procedure is the same except: 1) αIIbβ3 is allowed to adhere in the presence of either eptifibatide (10 μM), RGDS (10 μM; Rockefeller University Proteomics Resource Center), the Compounds (100 µM), or DMSO (1%); 2) wells are washed 10 times after αIIbβ3 adhesion; and 3) absorbance is determined at 655 nm after 10 min.

Platelet Adhesion Under Shear Stress. A cone and plate system (Diamed, Cressier, Switzerland) is used to assess the effect of the Compounds on platelet deposition under shear stress. 0.25 ml of citrated whole blood is incubated with nothing, DMSO (0.5%), the Compounds (50 µM), or tirofiban (10 µM) for 15 min at 22° C. and placed in polystyrene wells (16 mm diameter, Nunc). A constant uniform shear force of 1800 $s^{-1}$ was applied across the well using a teflon cone for 2 min at 22° C. Wells are washed with buffer, fixed with 1% paraformaldehyde, stained with Wright's Stain (Sigma-Aldrich), and analyzed for platelet adhesion using a 20× objective in an inverted microscope (IX51, Olympus, Center Valley, Pa.). Platelet adhesion is assessed by measuring the area occupied by platelets in each of four uniformly selected viewing areas in duplicate wells using image analysis software (SlideBook, Intelligent Imaging Innovations, Denver, Colo.).

Fluorescent RGD Peptide Binding to αIIbβ3. A fluorescent cyclic RGD-containing pentapeptide [5(6)-carboxyfluorescein-c(KRGDf)] is used. 300 nM αIIbβ3 is prepared in 0.15 M NaCl, 50 mM Tris/HCl containing 1 mM $MnCl_2$, and buffer, the Compounds, DMSO, or tirofiban is added and after 10 min at 22° C., fluorescence polarization is measured using a fluorescence polarization microplate reader (Envision, PerkinElmer). Polarization is expressed in millipolarization units (mP). Values obtained in the presence of tirofiban are taken as background, and all other values are expressed as a percentage of the mP value observed in the presence of buffer alone (no inhibitor).

Screening. The primary screen identifies 102 compounds out of a total 33,264 compounds screened (0.31% hit rate), that inhibit platelet adhesion to immobilized fibrinogen by more than 50% on two days of screening. Of these compounds, 32 inhibit platelet adhesion by more than 60%, and 9 inhibit adhesion by more than 70%. All 102 compounds identified in the primary screen are next screened for their ability to inhibit platelet aggregation induced by 5 µM ADP. Secondary screening identified compounds of the present invention with significant inhibitory activity, with the preferred compound of the present invention reducing the initial slope of aggregation by 84%.

Platelet Aggregation. Compounds of the present invention are tested for their ability to inhibit platelet aggregation via addition of 5 µM ADP over a range of concentrations. The Compounds are also tested for their ability to inhibit platelet aggregation via the addition of other agonists. The preferred compound of the present invention inhibits the aggregation of platelets in citrated PRP induced by 5 µM ADP, 5 µM TRAP, and 1 mM arachidonic acid with $IC_{50}$ values of 13±5 µM, 29±6 µM, and 8.5±5.7 µM respectively, and inhibits the aggregation of washed platelets induced by 5 µM TRAP with an $IC_{50}$ of 3.4±0.4 µM (n=3). The preferred Compound (100 µM) completely inhibits platelet aggregation in PRP induced by collagen (2 µg/ml). Like the αIIbβ3-specific mAb 10E5, the preferred Compound does not inhibit the initial slope of ristocetin-induced (1.8 mg/ml) agglutination/aggregation of PRP, but does inhibit the later phase of aggregation (data not shown). In the GPIb-specific mAb 6D1 (20 µg/ml) completely abolishes the initial wave of ristocetin-induced agglutination.

Untreated platelets and platelets treated with DMSO (0.5%) adhere to polystyrene wells when subjected to shear. Compared to the area occupied by platelets in samples treated with DMSO, the preferred Compound (50 µM) inhibits the deposition by 87±10% (p<0.025) and tirofiban (10 µM) inhibits the deposition by 99±1% (p<0.015, n=3).

Platelet Adhesion to Collagen (Imaging). Compounds are tested for their ability to inhibit platelet adhesion to collagen adsorbed to a cover glass. Compounds of the present invention are shown to abolish platelet adhesion at ≥50 µM. Confocal microscopy of adherent platelets in the presence of either no compound or DMSO reveals platelet aggregates associated with adherent platelets typical of adhesion to collagen, wherein platelets adhere initially via collagen interaction with integrin α2β1, and additional platelets are recruited to form aggregate via αIIbβ3 interaction with fibrinogen released from platelet α-granules. Accordingly, in the presence of the mAb 10E5 (20-40 µg/ml), which inhibits αIIbβ3 ligand binding, this clustering is not observed. In the presence of Compounds of the present invention (50-250 µM), adherent platelets resemble those adherent in the presence of mAb 10E5, where aggregate formation is not observed. Platelet adhesion to adsorbed collagen in microtiter plates yields equivalent results when assessed for the relative number of adherent platelets in each condition. Concomitant treatment of platelets with mAb 10E5 and increasing concentrations of compounds of the present invention (20-100 µM) does not significantly alter platelet adhesion relative to treatment with mAb 10E5 or compounds of the present invention alone, indicating similar or identical mechanisms of action.

mAb Binding. Compounds are tested for their effect on the binding of various αIIb, β3, and αIIbβ3-specific mAbs to resting platelets. The LIBS (Ligand Induced Binding Site)-specific mAbs AP5, LIBS1, and PMI-1 are among the mAbs tested. First, resting platelets are washed and incubated with compounds of the present invention before adding fluorescently labeled mAbs. The combined results from mAb binding experiments are shown in Table 1. 2-ethyl-7-(piperazin-1-yl)-5H-[1,3,4]thiadiazolo-[3,2-a]pyrimidin-5-one is shown to increase binding of the αIIb LIBS mAb PMI-1 by 44% relative to tirofiban while untreated platelets increases binding by 11% relative to tirofiban. The binding of other mAbs β3 LIBS-specific mAbs LIBS-1 and AP5 in the presence of 2-ethyl-7-(piperazin-1-yl)-5H-[1,3,4]thiadiazolo-[3,2-a]pyrimidin-5-one do not differ significantly from binding to untreated platelets.

The Preferred Compound Inhibits Fibrinogen Binding to Platelets, Recombinant Cells, and Purified αIIbβ3 and has no "Priming" Activity. The preferred Compound inhibits fibrinogen binding to platelets induced by the activating LIBS mAb AP5 with an $IC_{50}$ of 29±2 µM (n=3), a value similar to its $IC_{50}$ for inhibiting AP5-induced fibrinogen binding to HEK293 cells (21±0.3 µM; n=3). Fibrinogen binds to purified αIIbβ3 in microtiter plates in both the presence and the absence of 1% DMSO or a functionally inactive derivative of the preferred compound in which the piperazine group is altered. The binding is blocked by preferred compound ($IC_{50}$ 1.6±0.4 µM, n=3), tirofiban, and mAb 10E5. The αIIbβ3-activating mAb AP5 increased fibrinogen binding to purified αIIbβ3 in the presence of buffer, DMSO or the preferred compound derivative, but mAb AP5 does not increase fibrinogen binding to purified αIIbβ3 in the presence of the preferred compound, tirofiban, or mAb 10E5.

In experiments designed to assess the ability of different compounds to enhance fibrinogen binding to purified αIIbβ3 (priming), transient exposure of αIIbβ3 to eptifibatide or RGDS peptide results in increased fibrinogen binding [150±31% (p<0.02) and 130±7% (p<0.001), respectively] compared to untreated αIIbβ3. In sharp contrast, pretreatment with DMSO or the preferred compound does not increase fibrinogen binding.

HEK293 Cell Adhesion to Fibrinogen. HEK293 cells expressing αIIbβ3 adhere to high density immobilized fibrinogen (50 µg/ml) in microtiter plates in the presence of 2 mM $Ca^{2+}$/1 mM $Mg^{2+}$ with or without treatment with 1% DMSO as a vehicle control. 100 µM 2-ethyl-7-(piperazin-1- yl)-5H-[1,3,4]thiadiazolo-[3,2-a]pyrimidin-5-one inhibits cell adhesion by 53±4%. The mAb 10E5 abolishes cell adhesion at 20 μg/ml.

CS1 Cell Adhesion to Vitronectin. Untreated αVβ3-expressing CS1 cells adhere to immobilized vitronectin in microtiter plate wells in the presence of $Mg^{2+}$ as do cells treated with 1% DMSO (vehicle control), 20 μg/ml 10E5, or 100 μM 2-ethyl-7-(piperazin-1-yl)-5H-[1,3,4]thiadiazolo-[3,2-a]pyrimidin-5-one. Cells treated with 20 μg/ml 7E3 do not adhere to vitronectin.

Fluorescent Fibrinogen Binding. Compounds are tested for their ability to inhibit fibrinogen binding to platelets and αIIbβ3-expressing HEK293 cells brought about by incubation with the αIIbβ3 activating LIBS mAb AP5 at 60 μg/ml. In these experiments, compounds of the present invention are shown to inhibit fibrinogen binding to platelets with IC50s of 20-29±7 μM. Fibrinogen binding to HEK293 cells is similarly inhibited by these compounds.

TABLE 1

| Monoclonal Antibody | Specificity | mAb Binding (% of tirofiban) | |
|---|---|---|---|
| | | Untreated Platelets | Preferred Compound |
| PMI-1 | αIIb | 11 ± 4.1 | 44 ± 8.7 |
| LIBS-1 | β3 | 9.0 ± 3.1 | 5.7 ± 6.3 |
| AP5 | β3 | 19 ± 6.2 | 26 ± 5.9 |

What is claimed is:

1. A method for inhibiting or reducing platelet aggregation and/or adhesion comprising administering to a subject in need thereof an effective amount of a compound of formula I-C:

Compound I-C wherein:
i) A is S, N, C or O;
ii) X is a single bond-or optionally substituted and saturated or unsaturated $C_1$-$C_4$alkylene, $C_3$-$C_{10}$cycloalkylene optionally containing one or more heteroatoms selected from a group consisting of O or N, —N($R_6$)— or —$C_1$-$C_4$alkyl-N($R_6$)—;
iii) Y is a single bond or optionally substituted and saturated or unsaturated $C_1$-$C_4$ alkylene, optionally substituted -aryl-, -arylalkylene-, -heteroaryl-, —C(O)—, —N($R_6$)C(O)—, —$R_3$C(O)—, —$R_3$-alkylamido- or —$R_3$—NHC(O)—;
iv) $R_1$ is $C_1$-$C_4$alkyl;
v) $R_3$ is H or optionally substituted and saturated or unsaturated $C_1$-$C_4$alkyl, optionally substituted ($R_6$)N—, —($R_4$)($R_5$)N—, —N($R_4$)($R_5$)—$C_1$-$C_4$alkyl-, aryl, heteroaryl, aryl$C_1$-$C_4$alkyl, heteroaryl$C_1$-$C_4$alkyl, or $C_3$-$C_8$cycloalkyl optionally containing one or more heteroatoms selected from a group consisting of O or N;
vi) $R_4$ and $R_5$ are linked together via a covalent bond so as to form a $C_3$-$C_8$cycloalkylene containing a nitrogen atom;
vii) $R_6$ is H, $C_1$-$C_4$alkyl, aryl or aryl$C_1$-$C_4$alkyl, in free or pharmaceutically acceptable salt form;
such that platelet aggregation and/or adhesion is reduced.

2. A method for the treatment or prophylaxis of a thrombotic disorder selected from a group consisting of stroke, myocardial infarction, unstable angina, abrupt closure following angioplasty or stent placement, thrombosis induced by peripheral vascular surgery, peripheral vascular disease and thrombotic disorders resulting from atrial fibrillation or inflammation, comprising administering to a subject in need thereof an effective amount of a Compound of Formula I-C:

Compound I-C wherein:
i) A is S, N, C or O;
ii) X is a single bond or optionally substituted and saturated or unsaturated $C_1$-$C_4$ alkylene, $C_3$-$C_{10}$cycloalkylene optionally containing one or more heteroatoms selected from a group consisting of O or N, —N($R_6$)— or —$C_1$-$C_4$alkyl-N($R_6$)—;
iii) Y is a single bond or optionally substituted and saturated or unsaturated $C_1$-$C_4$alkylene, optionally substituted -aryl-, -arylalkylene-, -heteroaryl-, —C(O)—, —N(R$_6$)C(O)—, —R$_3$C(O)—, —R$_3$-alkylamido- or —R$_3$—NHC(O)—;

iv) R$_1$ is C$_1$-C$_4$alkyl;

v) R$_3$ is H or optionally substituted and saturated or unsaturated C$_1$-C$_4$alkyl, optionally substituted (R$_6$)N—, —(R$_4$)(R$_5$)N—, —N(R$_4$)(R$_5$)—C$_1$-C$_4$alkyl-, aryl, heteroaryl, arylC$_1$-C$_4$alkyl, heteroarylC$_1$-C$_4$alkyl, or C$_3$-C$_8$cycloalkyl optionally containing one or more heteroatoms selected from a group consisting of O or N;

vi) R$_4$ and R$_5$ are linked together via a covalent bond so as to form a C$_3$-C$_8$cycloalkylene containing a nitrogen atom;

vii) R$_6$ is H, C$_1$-C$_4$alkyl, aryl or arylC$_1$-C$_4$alkyl, in free or pharmaceutically acceptable salt form.

3. The method according to claim 1, wherein said Compound is 2-ethyl-7-(piperazin-1-yl)-5H-[1,3,4]thiadiazolo[3,2-a]pyrimidin-5-one in free or pharmaceutically acceptable salt form.

4. The method according to claim 2, further comprises administering an effective amount of at least one therapeutic agent selected from a group consisting of anti-coagulant, antiplatelet, and fibrinolytic agents in conjunction with the compound as described in claim 2.

5. The method according to claim 4, wherein said therapeutic agent is selected from a group consisting of heparin, low molecular weight heparins, bivalirudin, Fondaparinux, warfarin, Acenocoumarol, Phenprocoumon, Phenindione, Abbokinase (urokinase), streptokinase, alteplase, retaplase, tenecteplase, prasugrel, aspirin, ticlopidine, clopidogrel, abciximab, eptifibatide and tirofiban.

6. The method according to claim 5 wherein said therapeutic agent is heparin.

7. The method according to claim 2, wherein said Compound is 2-ethyl-7-(piperazin-1-yl)-5H-[1,3,4]thiadiazolo[3,2-a]pyrimidin-5-one in free or salt form.

8. The method according to claim 2, wherein R$_3$ is selected from a group consisting of cyclopentyl, cyclohexyl, piperazinyl, methylpiperazinyl, ethylpiperazinyl, propylpiperazinyl, piperidinyl, azepanyl, pyrrolidinyl, imidazolidinyl, methylpyrrolidinyl, ethylpyrrolidinyl, morpholinyl and tetrahydroquinolinyl, in free or pharmaceutically acceptable salt form.

9. The method according to claim 2, wherein R$_4$ and R$_5$ are linked together via a covalent bond so as to form a piperidinylene, in free or pharmaceutically acceptable salt form.

10. The method according to claim 2, wherein A is S; X is a single bond; and Y is a single bond; in free or pharmaceutically acceptable salt form.

11. The method according to claim 7, further comprises administering an effective amount of at least one therapeutic agent selected from a group consisting of anti-coagulant, antiplatelet, and fibrinolytic agents in conjunction with the compound as described in claim 7.

12. The method according to claim 7, further comprises administering an effective amount of at least one therapeutic agent selected from a group consisting of heparin, low molecular weight heparins, bivalirudin, fondaparinux, warfarin, acenocoumarol, phenprocoumon, phenindione, urokinase, streptokinase, alteplase, retaplase, tenecteplase, prasugrel, aspirin, ticlopidine, clopidogrel, abciximab, eptifibatide and tirofiban.

13. The method according to claim 11 wherein said therapeutic agent is heparin.

14. The method according to claim 10, further comprises administering an effective amount of at least one therapeutic agent selected from a group consisting of anti-coagulant, antiplatelet, and fibrinolytic agents in conjunction with the compound as described in claim 10.

15. The method according to claim 10, further comprises administering an effective amount of at least one therapeutic agent selected from a group consisting of heparin, low molecular weight heparins, bivalirudin, fondaparinux, warfarin, acenocoumarol, phenprocoumon, phenindione, urokinase, streptokinase, alteplase, retaplase, tenecteplase, prasugrel, aspirin, ticlopidine, clopidogrel, abciximab, eptifibatide and tirofiban.

16. The method according to claim 15, wherein said therapeutic agent is heparin 17. the method according to claim 1, wherein A is S; X is a single bond; and Y is a single bond; in free or pharmaceutically acceptable salt form.

* * * * *